(12) United States Patent
Ziraknejad et al.

(10) Patent No.: US 10,403,402 B2
(45) Date of Patent: Sep. 3, 2019

(54) METHODS AND SYSTEMS FOR ACCESSING AND MANIPULATING IMAGES COMPRISING MEDICALLY RELEVANT INFORMATION WITH 3D GESTURES

(71) Applicant: The University of British Columbia, Vancouver (CA)

(72) Inventors: Nima Ziraknejad, North Vancouver (CA); Behrang Homayoon, Vancouver (CA); Peter Lawrence, Vancouver (CA); David Ming-Teh Liu, Point Roberts, WA (US)

(73) Assignee: The University of British Columbia, Vancouver (CA)

( * ) Notice: Subject to any disclaimer, the term of this patent is extended or adjusted under 35 U.S.C. 154(b) by 103 days.

(21) Appl. No.: 15/432,749

(22) Filed: Feb. 14, 2017

(65) Prior Publication Data

US 2017/0228104 A1 Aug. 10, 2017

Related U.S. Application Data

(63) Continuation of application No. PCT/CA2015/050764, filed on Aug. 13, 2015.
(Continued)

(51) Int. Cl.
*G06F 9/48* (2006.01)
*G16H 40/63* (2018.01)
(Continued)

(52) U.S. Cl.
CPC ............. *G16H 40/63* (2018.01); *A61B 90/37* (2016.02); *A61G 13/10* (2013.01); *G06F 3/017* (2013.01);
(Continued)

(58) Field of Classification Search
CPC ...... G06F 3/0425; G06F 19/321; G06F 3/017; G06F 3/0482; G06F 3/04845;
(Continued)

(56) References Cited

U.S. PATENT DOCUMENTS 8,230,367 B2 7/2012 Bell et al.
2008/0263479 A1 10/2008 Bloem et al.
(Continued)

OTHER PUBLICATIONS

Justin H. Tan et al: "Informatics in Radiology: Developing a Touchless User Interface for Intraoperative Image Control during Interventional Radiology Procedures", Radiographics., vol. 33, No. 2, Apr. 30, 2013 (Apr. 30, 2013), pp. E61-E70.
(Continued)

*Primary Examiner* — Jennifer N To
*Assistant Examiner* — K C Chen
(74) *Attorney, Agent, or Firm* — Todd A. Rattray; Oyen Wiggs Green & Mutala LLP

(57) ABSTRACT

A system permits a medical practitioner to interact with medically relevant information during a medical procedure. The system comprises: a projector for projecting a user interface menu image onto a projection surface; a three-dimensional optical imaging system for capturing three-dimensional location information for objects in a sensing volume which includes the projection surface; and a controller connected to receive the three-dimensional location information from the three-dimensional optical imaging system and configured to interpret one or more gestures made by the practitioner in a space between the three-dimensional optical imaging system and the projection surface based on a location of the gesture relative to the projected user interface menu image. The controller is connectable to a display to cause the display to render images and is configured to cause the display to render an
(Continued)

image comprising medically relevant information, the medically relevant information based at least in part on the interpreted gesture.

17 Claims, 9 Drawing Sheets

Related U.S. Application Data

(60) Provisional application No. 62/038,157, filed on Aug. 15, 2014.

(51) Int. Cl.
*G06F 19/00* (2018.01)
*G06F 3/01* (2006.01)
*G06F 3/0488* (2013.01)
*G16H 40/60* (2018.01)
*A61B 90/00* (2016.01)
*A61G 13/10* (2006.01)
*G06F 3/042* (2006.01)
*G06F 3/0482* (2013.01)
*G06F 3/0484* (2013.01)
*G06F 3/0485* (2013.01)

(52) U.S. Cl.
CPC .......... *G06F 3/0425* (2013.01); *G06F 3/0482* (2013.01); *G06F 3/0485* (2013.01); *G06F 3/04845* (2013.01); *G06F 3/04883* (2013.01); *G06F 19/321* (2013.01); *G16H 40/60* (2018.01)

(58) Field of Classification Search
CPC ... G06F 3/0485; G06F 3/04883; G16H 40/63; G16H 40/60; A61B 90/37; A61G 13/10
See application file for complete search history.

(56) References Cited

U.S. PATENT DOCUMENTS

| | | |
|---|---|---|
| 2009/0021475 A1 | 1/2009 | Steinle et al. |
| 2009/0077504 A1 | 3/2009 | Bell et al. |
| 2009/0228841 A1* | 9/2009 | Hildreth ................ G06F 3/0304 715/863 |
| 2011/0181553 A1* | 7/2011 | Brown .................. G06F 3/0425 345/175 |
| 2013/0076620 A1* | 3/2013 | Fukano .................. G03B 21/14 345/156 |
| 2013/0265219 A1 | 10/2013 | Sato |
| 2013/0321346 A1 | 12/2013 | Tyler et al. |
| 2014/0049465 A1 | 2/2014 | Tremaine et al. |
| 2014/0177909 A1 | 6/2014 | Lin et al. |
| 2014/0195983 A1 | 7/2014 | Du et al. |
| 2015/0208019 A1* | 7/2015 | Stewart ................. G06F 1/1673 348/745 |

OTHER PUBLICATIONS

Wachs et al. "A gesture-based tool for sterile browsing of radiology images." Journal of the American Medical Informatics Association vol. 15, No. 3, 321-323, May/Jun. 2008 (Jun. 2008).

Wachs et al., "Real-time hand gesture interface for browsing medical images." International Journal of Intelligent Computing in Medical Sciences & Image Processing, vol. I. No. 3, 175-185. Mar. 3, 2007.

Ahmed et al., "Geometric Correction for Uneven Quadric Projection Surfaces Using Recursive Subdivision of Bézier Patches". ETRI Journal, vol. 35, No. 6, Dec. 2013, pp. 1115-1125.

Andriole et al., "Optimizing Analysis, Visualization, and Navigation of Large Image Data Sets: One 5000-Section CT Scan Can Ruin Your Whole Day". Department of Radiology, vol. 259: No. 2—May 2011, pp. 346-362.

Breuer et al., "Hand Gesture Recognition With a Novel IR Time-of-Flight Range Camera—A Pilot Study". Mirage 2007, LNCS 4418, pp. 247-260.

Johnson et al., "Exploring the Potential for Touchless Interaction in Image-Guided Interventional Radiology". CHI 2011-Session: Doctor-Patient Care, May 7-12, 2011, pp. 3323-3332.

Van den Bergh et al., "Haarlet-based Hand Gesture Recognition for 3D Interaction". Competence Center of Digital Design Modeling (DDM) at ETH Zurich. 2009, 8 pages.

Ziraknejad, et al., "The Effect of Time-of-Flight Camera Integration Time on Vehicle Driver Head Pose Tracking Accuracy". 2012 IEEE International Conference on Vehicular Electronics and Safety, Jul. 24-27, 2012.

"Natural User Interfaces for Healthcare". Website found at: http://www.tedcas.com; web page archive May 18, 2014.

"Take Control of Your Operating Room". Website found at: http://www.gestsure.com; web page archive Jul. 29, 2014.

* cited by examiner ated States (US 10,403,402 B2)

METHODS AND SYSTEMS FOR ACCESSING AND MANIPULATING IMAGES COMPRISING MEDICALLY RELEVANT INFORMATION WITH 3D GESTURES

RELATED APPLICATIONS

This application is a continuation of Patent Cooperation Treaty (PCT) application No. PCT/CA2015/050764 filed 13 Aug. 2015 entitled METHODS AND SYSTEMS FOR PERFORMING MEDICAL PROCEDURES AND FOR ACCESSING AND/OR MANIPULATING MEDICALLY RELEVANT INFORMATION, which in turn claims the benefit of the priority of, and the benefit under 35 USC § 119 of, U.S. application No. 62/038,157 filed 15 Aug. 2014. Both PCT application No. PCT/CA2015/050764 and U.S. application No. 62/038,157 are hereby incorporated by reference herein.

TECHNICAL FIELD

The technology disclosed herein relates to methods and systems for performing medical procedures and to methods and systems for interacting with medically relevant information which may be desirable to have during medical procedures.

BACKGROUND

There is a desire to provide medical practitioners (e.g. surgeons, interventional radiologists, nurses, medical assistants, other medical technicians and/or the like) with access to, the ability to manipulate and/or the ability to otherwise interact with medically relevant information during the performance of medical procedures (e.g. surgical procedures and/or the like). Such desired medical information may include, by way of non-limiting example, radiological images, angiography images, other forms of images of the patient's body, other information relevant to a patient undergoing the medical procedure, other information relevant to the procedure itself, other information related to the condition being treated and/or the like. Such desired medical information may be procured prior to performing the procedure and/or during performance of the procedure and may allow medical practitioners to formulate or alter their therapeutic plan during image-guided medical procedures.

Currently, intra-procedural access to, manipulation of and/or interaction with radiological images takes place on computer workstations in control rooms located outside of the surgical sterile environment. Such workstations may access, via suitable network communications or other digital access techniques, archives of image data pertaining to a patient by accessing picture archiving and communication systems (PACS); digital imaging and communications in medicine systems (DICOM), hospital information systems (HIS), radiological information systems (RIS) and/or the like. Such workstations may then display individual images on a suitable display and may permit manipulation of the images via a conventional computer-based user interface—e.g. using a mouse and keyboard and a software-implemented user interface. Because the workstations are located outside of the surgical sterile environment, radiologists wanting to access various images typically have to either: (a) scrub out of a procedure on one or more occasions during the procedure; or (b) delegate the task of accessing the desired image(s) to a technologist, who then has to operate the workstation under the direction of the radiologist.

In case (a), the need to move back and forth between the non-sterile control room and the sterile surgical environment for purposes of image navigation and interpretation may: increase the risk of contaminating the sterile environment by inadvertently transferring contaminants from the non-sterile control room into the sterile environment; extend the time required to complete the surgery, thereby increasing procedural costs; and/or interrupt the medical practitioner's cognitive focus, thereby increasing the medical risk for the patient. In case (b), close communication between the radiologists and the technician operating the workstation is typically required. Communication of relevant information (e.g. how much to move or enlarge an image) is difficult and time-consuming and may require several iterations. This process may be made more difficult by the need to use different software platforms, to navigate through vendor-specific multi-layered menus, and to interact with volumetric images using a keyboard and mouse.

With an increasing reliance on numerous radiological images for intra-procedural planning and confirmation of targeted therapy, there is a general desire to develop solutions that improve the radiologist's ability to rapidly access, manipulate and/or otherwise interact with large amounts of image information (and/or other medically relevant information) in an intuitive, comprehensive, and timely manner while in the sterile environment.

The foregoing examples of the related art and limitations related thereto are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

Aspects of the invention provide systems and methods for permitting medical practitioners to access, manipulate and/or otherwise interact with medically relevant information during a medical procedure using gestures (e.g. touchless gestures) to interact with a projected user interface menu image. The gestures may be based on the configuration, location or movement of a practitioner's hand. The gestures may be interpreted based on the location of the gesture (e.g. the location of the practitioner's hand) relative to the projected user interface menu image (and/or the projection surface on which user interface menu image is projected). The gestures may additionally or alternatively be based on the configuration or movement of the gesture (e.g. the configuration or movement of the practitioner's hand). Such gesture movement or configuration may be relative to the projected user interface menu image (and/or the projection surface on which the user interface image is projected). Such systems and methods provide this capability without the need for the medical practitioner to scrub out of the sterile environment in which the procedure is being performed and without the need to communicate with technicians located outside of the sterile environment. By way of example, medically relevant information accessed, manipulated and/or otherwise interacted with during a medical procedure may include: radiological images, angiography images, other forms of images of the patient's body or other information relevant to a patient undergoing the medical procedure, to the procedure itself and/or the like. The system may comprise a projection device for projecting a user interface menu image onto a projection surface suitable for being viewed by the medical practitioner, the projection surface located in the sterile environment and a three-dimensional (3-D) optical imaging sensor or system for capturing 3-D information relating to the manner in which the medical practitioner interacts with the projected user interface menu image (e.g. using gestures in locations relative to the projected user interface menu image). Non-limiting examples of such 3-D optical sensors/systems include a so-called time-of-flight (TOF) imaging system (also referred to as a range imaging system), a phase modulating 3-D optical sensor system, 3D optical sensors which are based on structured light mechanisms (e.g. speckle patterns) and/or the like.

A controller connected to the 3-D optical imaging system may interpret gestures comprising movements, configurations and/or locations of one of the medical practitioner's hands relative to the user interface menu image and/or relative to the projection surface on which the user interface menu image is projected. Based on the interpretation of such gestures, the controller may cause a display to render an image (or other information) that is visible to the medical practitioner. The displayed image may comprise an image or a portion of an image from a library of images relating to the patient on whom the procedure is being performed. Based on the interpretation of such gestures, the controller may manipulate the displayed image. For example, such manipulation may comprise zooming in or out with respect to a particular displayed image, panning or otherwise moving a displayed portion of a particular displayed image; adjusting brightness, contrast and/or color parameters of a particular displayed image; scrolling through a library of images to select a new image for display; and/or the like.

The projection surface may be generally horizontal. The medical practitioner may interact with the system using gestures of one (or both) of their hands in the space between the generally horizontal projection surface and 3-D optical imaging system and such gestures may be interpreted based on the location of the practitioner's hand relative to the projected user interface menu image and/or relative to the projection surface on which the user interface menu image is projected. The projection surface may comprise a portion of the operating table on which the patient on whom the procedure is being performed is located. The size of the projected user interface menu image may be adjustable (based on data acquired by the 3-D optical imaging system) so that the projected user interface menu image fits on the portion of the operating table (e.g. without crossing over the operating table edges). The projection surface may be irregular (e.g. non-planar or generally, but not perfectly, horizontal) based, by way of non-limiting example, on the presence of the patient's body, the state of any projection surface (e.g. operating table) coverings and/or the like. A profile of the irregularity of the projection surface may be determined based on data acquired by the 3-D optical imaging system and the projected user interface menu image may be adjusted to compensate for the irregularity of the projection surface. The reflectivity and/or the color of the projection surface may be estimated based on data acquired by the 3-D optical imaging system or by some other suitable imaging system (e.g. a color camera) and the projected user interface menu image may be adjusted to compensate for the reflectivity and/or color of the projection surface.

Based on the interpretation of gestures, the controller may determine when to project the user interface and when to not project the user interface.

Other aspects of the invention provide systems comprising one or more processors, wherein the processors are configured to perform methods according to any aspects of the invention.

Other aspects of the invention comprise computer program products comprising computer-readable instructions embodied on non-transitory media. When executed by a suitable computer or processor, the computer-readable instructions cause the computer or processor to perform methods according to any aspects of the invention.

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

DESCRIPTION

Figure 1:
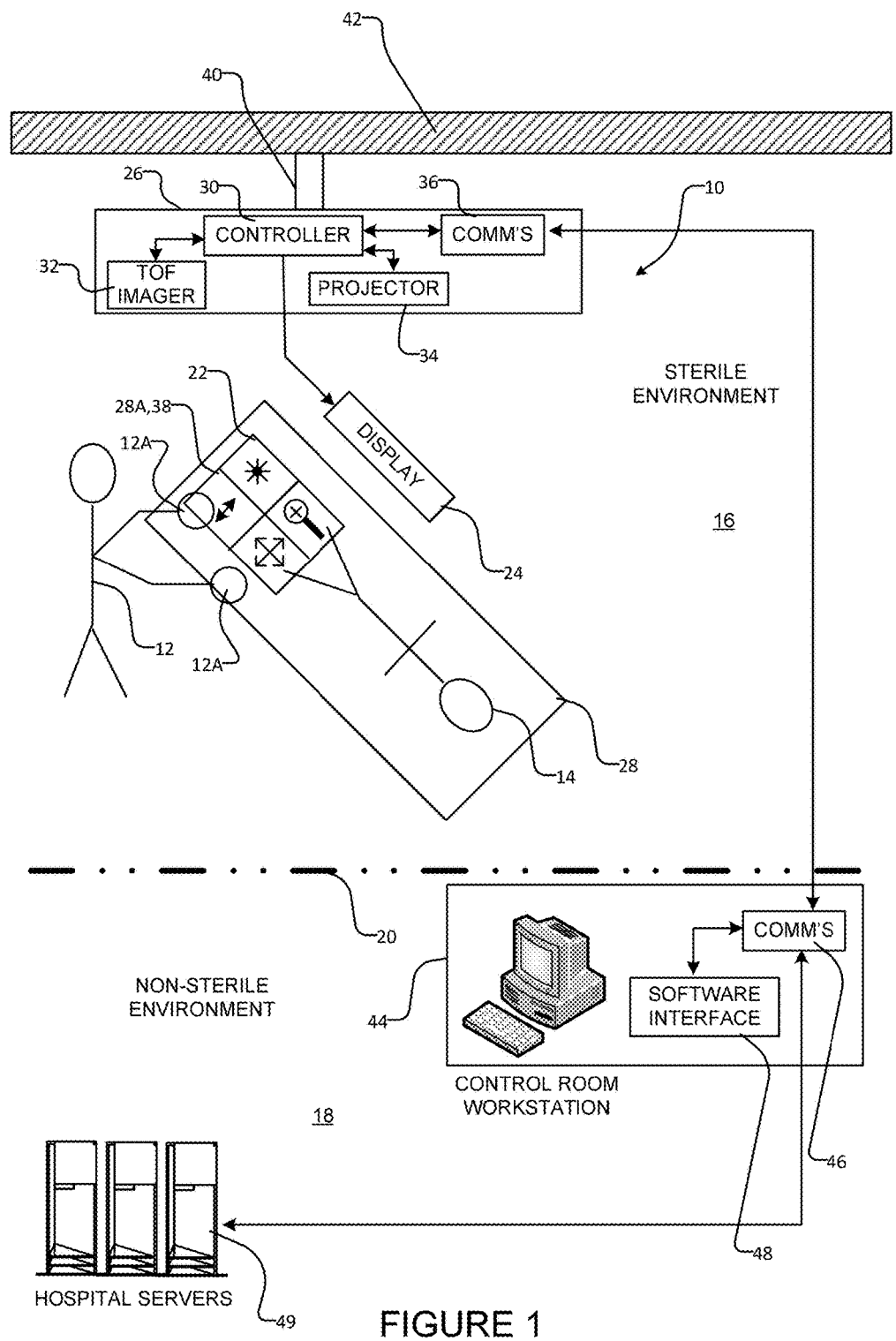
FIG. 1 is a schematic depiction of a system for performing medical procedures and for accessing, manipulating and/or otherwise interacting with medically relevant information according to a particular embodiment.

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

Aspects of the invention provide systems and methods for permitting medical practitioners to access, manipulate and/or otherwise interact with medically relevant information during a medical procedure using gestures (e.g. touchless gestures) to interact with a projected user interface menu image. The gestures may be based on the configuration, location or movement of a practitioner's hand. As used herein, unless the context dictates otherwise, references to gestures of a practitioner's hand(s) should be understood to include gestures based on one or more of the practitioner's fingers which are included in their hand(s). The gestures may be interpreted based on the location of the gesture (e.g. the location of the practitioner's hand) relative to the projected user interface menu image (and/or the projection surface on which user interface menu image is projected). The gestures may additionally or alternatively be based on the configuration or movement of the gesture (e.g. the configuration or movement of the practitioner's hand). Such gesture movement or configuration may be relative to the projected user interface menu image (and/or the projection surface on which the user interface image is projected). Such systems and methods provide this capability without the need for the medical practitioner to scrub out of the sterile environment in which the procedure is being performed and without the need to communicate with technicians located outside of the sterile environment. By way of example, medically relevant information accessed, manipulated and/or otherwise interacted with during a medical procedure may include: radiological images, angiography images, other forms of images of the patient's body or other information relevant to a patient undergoing the medical procedure, to the procedure itself and/or the like. The system may comprise a projection device for projecting a user interface menu image onto a projection surface suitable for being viewed by the medical practitioner, the projection surface located in the sterile environment and a three-dimensional (3-D) optical imaging sensor or system for capturing 3-D information relating to the manner in which the medical practitioner interacts with the projected user interface menu image (e.g. using gestures in locations relative to the projected user interface menu image). Non-limiting examples of such 3-D optical sensors/systems include a so-called time-of-flight (TOF) imaging system (also referred to as a range imaging system), a phase modulating 3-D optical sensor system and/or the like.

A controller connected to the 3-D optical imaging system may interpret gestures comprising movements, configurations and/or locations of one of the medical practitioner's hands relative to the user interface menu image and/or relative to the projection surface on which the user interface menu image is projected. Based on the interpretation of such gestures, the controller may cause a display to render an image (or other information) that is visible to the medical practitioner. The displayed image may comprise an image or a portion of an image from a library of images relating to the patient on whom the procedure is being performed. Based on the interpretation of such gestures, the controller may manipulate the displayed image. For example, such manipulation may comprise zooming in or out with respect to a particular displayed image, panning or otherwise moving a displayed portion of a particular displayed image; adjusting brightness, contrast and/or color parameters of a particular displayed image; scrolling through a library of images to select a new image for display; and/or the like.

The projection surface may be generally horizontal. The medical practitioner may interact with the system using gestures of one (or both) of their hands in the space between the generally horizontal projection surface and 3-D optical imaging system and such gestures may be interpreted based on the location of the practitioner's hand relative to the projected user interface menu image and/or relative to the projection surface on which the user interface menu image is projected. The projection surface may comprise a portion of the operating table on which the patient on whom the procedure is being performed is located. The size of the projected user interface menu image may be adjustable (based on data acquired by the 3-D optical imaging system) so that the projected user interface menu image fits on the portion of the operating table (e.g. without crossing over the operating table edges). The projection surface may be irregular (e.g non-planar or generally, but not perfectly, horizontal) based, by way of non-limiting example, on the presence of the patient's body, the state of any projection surface (e.g. operating table) coverings and/or the like. A profile of the irregularity of the projection surface may be determined based on data acquired by the 3-D optical imaging system and the projected user interface menu image may be adjusted to compensate for the irregularity of the projection surface. The reflectivity and/or the color of the projection surface may be estimated based on data acquired by the 3-D optical imaging system or by some other suitable imaging system (e.g. a color camera) and the projected user interface menu image may be adjusted to compensate for the reflectivity and/or color of the projection surface.

Based on the interpretation of gestures, the controller may determine when to project the user interface and when to not project the user interface.

FIG. 1 is a schematic depiction of a system 10 for performing medical procedures and for accessing, manipulating and/or otherwise interacting with medically relevant information according to a particular embodiment. System 10 permits a medical practitioner 12 to access, manipulate and/or otherwise interact with medically relevant information during a medical procedure being performed on patient 14 in a sterile environment 16. System 10 permits practitioner 12 to use gestures (e.g. touchless gestures) to interact with a projected user interface menu image 22 to access, manipulate and/or otherwise interact images which may be displayed on display 24. The gestures may be based on the configuration. location or movement of the practitioner's hand(s) 12A. Displayed images displayed on display 24 may contain medically relevant information, which may comprise: radiological images, angiography images, other forms of images of the patient's body, other information relevant to a patient undergoing the medical procedure, other information relevant to the procedure itself and/or the like. Display 24 may be easily viewable by the practitioner 12 in sterile environment 16 to allow the medical practitioner 12 to view the medical information provided by the displayed image. In the FIG. 1 schematic illustration, sterile environment 16 in which the medial procedure is being performed is separated from external environments 18 (e.g. potentially non-sterile environments) by notional line 20. In the illustrated embodiment, display 24 is located in sterile environment 16, although this is not necessary.

System 10 of the FIG. 1 embodiment, comprises user interface device 26 which may be supported in a location above an operating table (or bed) 28 on which patient 14 is located during the procedure or in some other suitable location. As will be described in more detail below, in the illustrated embodiment of FIG. 1, user interface device 26 comprises: a controller 30 for controlling the operation of user interface device 26; a 3-D optical imaging system 32 for capturing 3D information relating to the manner in which practitioner 12 interacts with a projected user interface menu image 22, including (for example) gestures of the medical practitioner 12; a projector 34 for projecting user interface menu image 22 onto a projection surface 38 suitable for being viewed and interacted with by medical practitioner 12; and a communications interface 36 for communications (e.g.

suitable network communications or other digital access techniques) with archives of medically relevant information. In some embodiments, user interface device 26 may be supported in the location above operating table 28 by an adjustable surgical arm 40 (e.g. mounted to ceiling 42, to a wall, to a floor-mounted support-column and/or the like), which may facilitate adjustment of the location of user interface device 26, corresponding adjustment of projection surface 38 onto which user interface menu image 22 is displayed and/or the imaging volume of 3-D optical sensing system 32. As discussed above, 3-D optical imaging system 32 captures 3D information relating to the manner in which practitioner 12 interacts with a projected user interface menu image 22, including (for example) gestures of the medical practitioner 12 (e.g. of the medical practitioner's hand(s) 12A). By way of non-limiting example, 3-D optical imaging system 32 may comprise a time-of-flight (TOF) imaging system (also referred to as a range imaging system), a phase modulating 3-D optical sensor system and/or some other system capable of providing similar 3-D information about a sensing volume For convenience, in the remainder of this description, 3-D optical imaging system 32 may be referred to as TOF sensor 32 without loss of generality.

Controller 30 may comprise components of a suitable computer system. In general, controller 30 may comprise any suitably configured processor, such as, for example, a suitably configured general purpose processor, graphics processing unit (GPU), graphics processing system, microprocessor, microcontroller, digital signal processor, field-programmable gate array (FPGA), other type of programmable logic device, pluralities of the foregoing, combinations of the foregoing, and/or the like. Controller 30 may be embedded (e.g. in user interface device 26, as is the case in the illustrated embodiment), although this is not necessary. Controller 30 has access to software which may be stored in computer-readable memory (not expressly shown) accessible to controller 30 and/or in computer-readable memory that is integral to controller 30. Controller 30 may be configured to read and execute such software instructions and, when executed by the controller 30, such software may cause controller 30 to implement some of the functionalities described herein. Controller 30 may comprise a plurality of networked computers or processors or pluralities of computers or processors which are otherwise in communication with one another.

Figure 2:
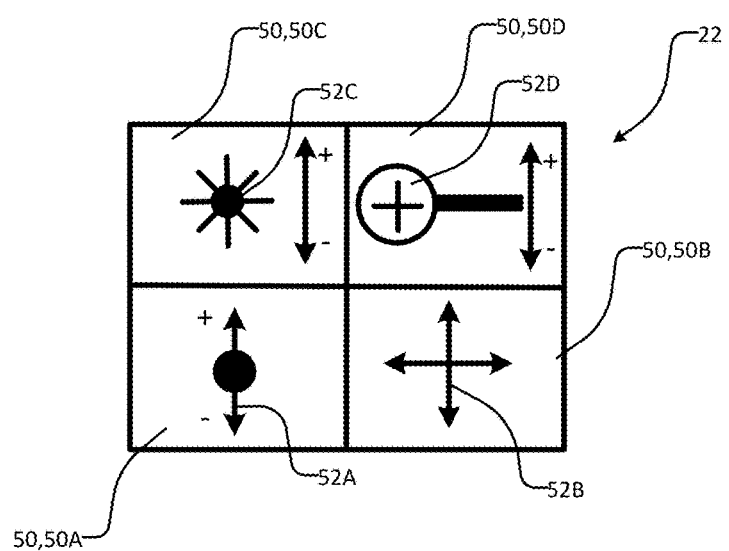
FIG. 2 is a schematic depiction of a user interface menu image which may be used with the FIG. 1 system in particular embodiments.

Controller 30 controls the operation of projector 34 to project a user interface menu image 22 onto a projection surface 38. In the illustrated embodiment, projection surface 38 is located in sterile environment 16 and is suitable for being viewed and interacted with by medical practitioner 12. In some embodiments, projection surface 38 may comprise a generally horizontal surface, although this is not necessary. In the case of system 10 of the illustrated FIG. 1 embodiment, projection surface 38 comprises a portion 28A of operating table 28 on which patient 14 is located. Selecting projection surface 38 to be a portion 28A of operating table 28 permits practitioner 12 to maintain his or her focus on patient 14. In some embodiments, projection surface 38 may be selected to be the horizontal surface of a side table and/or the like which may be located relatively close to the medical practitioner 12 performing or assisting with the procedure— e.g. the table on which the procedural equipment is located and/or the like. FIG. 2 shows a depiction of a user interface menu image 22 projected onto a projection surface 38 according to a particular embodiment. User interface menu image 22 comprises a plurality of user interface image sections 50. In the FIG. 2 embodiment, user interface menu image 22 comprises four user interface image sections 50A-50D, although in general user interface menu image 22 may comprise any suitable number of user interface image sections 50. User interface image sections 50 may each be associated with a corresponding functionality (or a corresponding menu selection) and may comprise graphical and/ or textual information relevant to their corresponding functionality/menu selection.

For example, in the case of the FIG. 2 embodiment, each of user interface image sections 50 is associated with a corresponding functionality. In particular: user interface image section 50A is associated with scrolling (e.g. between images for display on display 24) and shows a graphical icon 52A associated with this scrolling functionality; user interface image section 50B is associated with panning or moving around in a particular image being displayed on display 24 and shows a graphical icon 52B associated with this panning functionality; user interface image section 50C is associated with adjusting the brightness of a particular image being displayed on display 24 and shows a graphical icon 52C associated with this brightness adjustment functionality; and user interface image section 50D is associated with zooming in and out of a particular image being displayed on display 24 and shows a graphical icon 52D associated with this brightness adjustment functionality. It will be appreciated by those skilled in the art based on the description provided herein that other functionalities could be associated with user interface image sections 50 and that different numbers of user interface image sections 50 could be provided to enable different numbers of functionalities. In addition to or in the alternative to functionalities, user interface menu image 22 may comprise a more classical text-based or graphical menu, where one or more of user interface image sections 50 correspond to menu selections.

As will be explained in more detail below, system 10 provides practitioner 12 with the ability to interact with user interface menu image 22 by making suitable gestures to facilitate selection of one of user interface image sections 50 and selection of the corresponding functionality/menu selection. Within a selected functionality or selected menu selection, system 10 permits practitioner 12 to implement the selected functionality to access, manipulate and/or otherwise interact with the image(s) being displayed on display 24, to carry out an action corresponding to a menu selection (e.g. to activate a sub-menu) and/or the like. For example, system 10 permits practitioner 12 to select the scroll functionality associated with the user interface display section 50A of the FIG. 2 embodiment by using suitable gesture(s) to select image display section 50A and its corresponding scrolling functionality. Then, after such selection, system 10 permits practitioner 12 to cause scrolling between the images displayed on display 24 using suitable further gestures. In some embodiments, the gestures recognized by system 10 comprise gestures made by one (or both) of the hands 12A of practitioner 12.

Figure 3A:
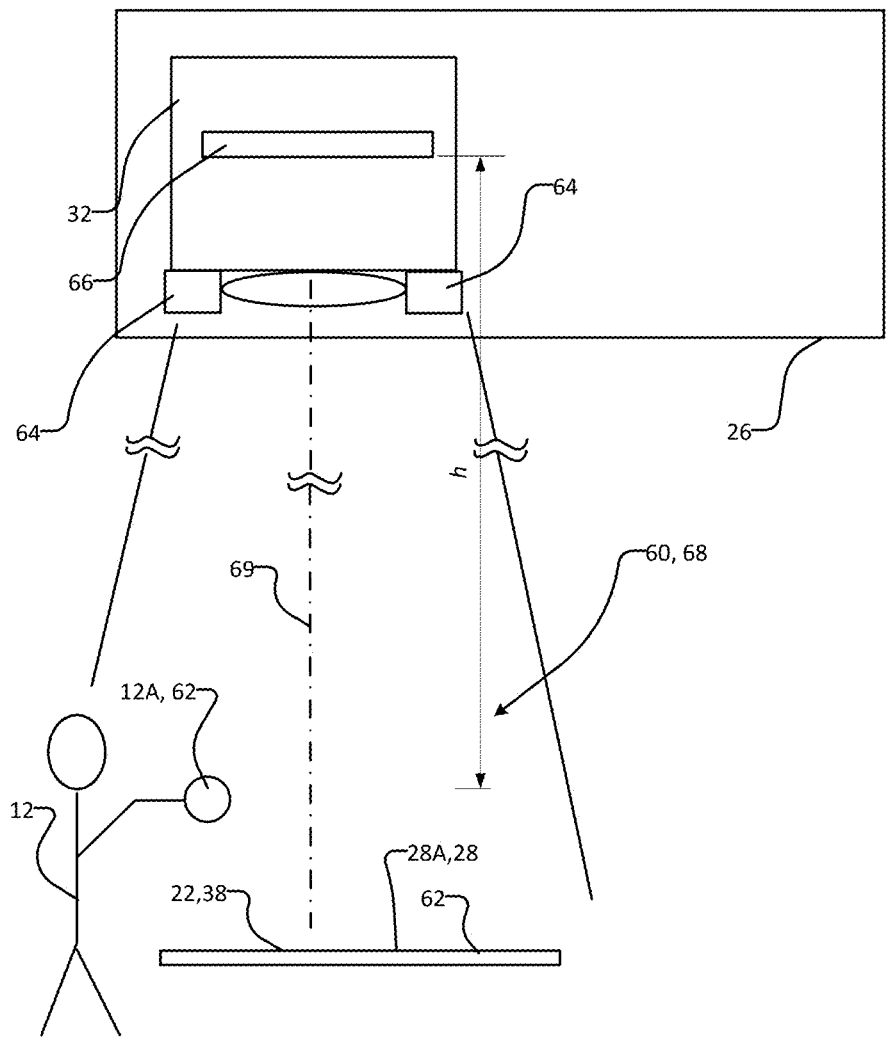
FIG. 3A shows a schematic depiction of a TOF imaging system (i.e. an example of a 3-D optical imaging system) which may be used in the system of FIG. 1 according to particular embodiments.

Controller 30 controls the operation of TOF imaging system 32. A TOF imaging system 32 is shown schematically in FIG. 3A. As is known in the art, TOF imaging systems 32 project electromagnetic radiation (e.g. IR radiation and/or near IR radiation) from one or more suitable radiation sources 64 (e.g. LEDs or lasers) into a sensor volume 60 and capture 3D image information corresponding to objects 62 in sensor volume 60 based on radiation reflected from such objects 62 and detected by a suitable photodetector 66 (e.g. comprising photodiode detector elements, CCD sensor elements, CMOS detector elements and/or the like). FIG. 3A shows the axial center 69 of TOF imaging system 32. System 10 may comprise any suitable TOF imaging system and/or device 32. As discussed elsewhere herein, system 10 is not specifically limited to using a TOF system 32 and the functionality of TOF system 32 can be provided by a phase modulating 3-D optical sensor system and/or some other 3-D optical imaging system capable of providing similar 3-D information about sensing volume 60.

TOF imaging system 32 returns a 3D point cloud comprising 3D locations of points on the surfaces of objects 62 located in its sensor volume 60. In the FIG. 1 embodiment, TOF imaging system 32 may be located or otherwise configured (e.g. oriented, configured using suitable optics and/or the like), such that sensor volume 60 includes projection surface 38 onto which user interface menu image 22 is projected by projector 34. The axial center 69 of sensor volume 60 may be configured to align generally with projection surface 38 (e.g. with a center of projection surface 38). As discussed above, projection surface 38 may comprise a portion 28A of operating table 28. With this configuration, TOF system 32 returns a point cloud comprising 3D locations of points on projection surface 38 onto which user interface menu image 22 is projected. TOF imaging system 32 may be similarly configured such that sensor volume 60 includes a space 68 above (or otherwise adjacent to) projection surface 38 and between projection surface 38 and TOF imaging system 32. For example, where projection surface 38 comprises a portion 28A of operating table 28, then space 68 may comprise a volume above operating table 28 and between operating table 28 and user interface device 26. With this configuration, practitioner 12 may make gestures with one (or both) of their hands 12A in space 68 and TOF imaging system 32 may detect the 3D locations of points on the surface of the practitioner's hand(s) 12A. Such 3D information about the practitioner's hand(s) 12A may be interpreted to be gestures through which practitioner 12 may interact with projected user interface menu image 22, as described in more detail below. This space 68 between projection surface 38 and TOF imaging system 32 may be convenient for use as a space in which practitioner 12 may make gestures with their hand(s) 12A, as this space 68 may be where the practitioner's hand(s) 12A are located for performance of the medical procedure, thereby providing ergonomic ease of interaction with system 10.

Figure 3B:
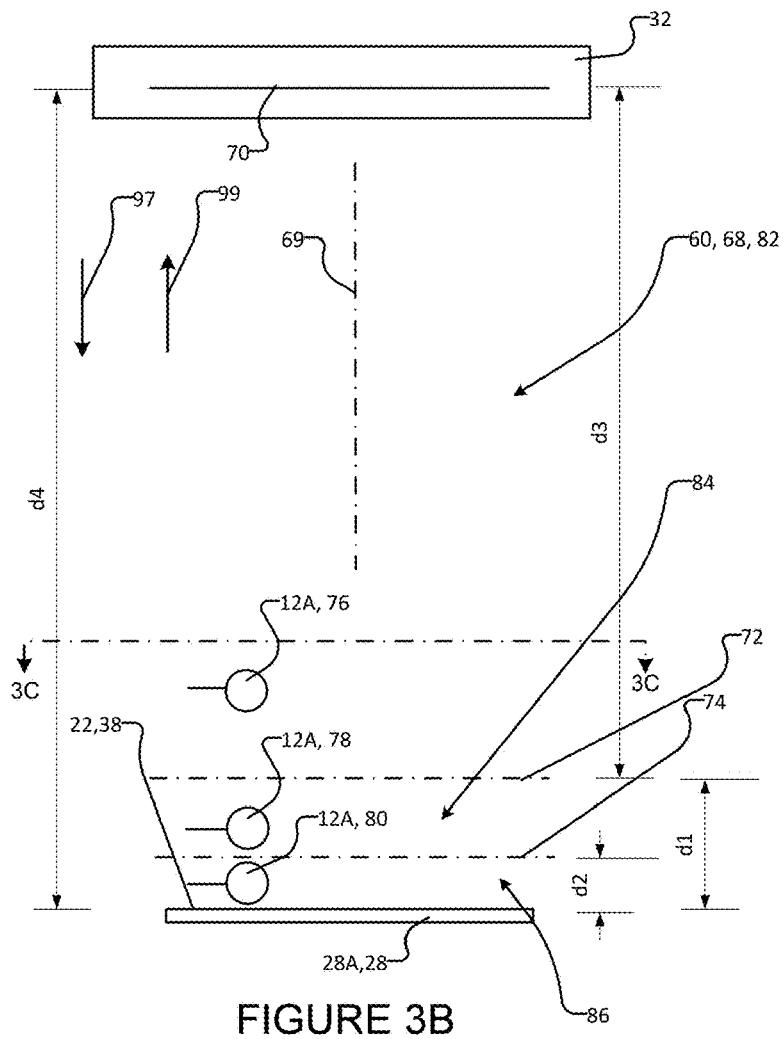
FIGS. 3B and 3C schematically depict the sensing volume of the FIG. 3A TOF imaging system.

FIG. 3B is a schematic side plan view of the sensing volume 60 of TOF imaging device 32 and space 68 (between projection surface 38 and TOF imaging device 32) according to a particular embodiment. Space 68 may be divided into a plurality of volume regions between a reference surface 70 of TOF imaging device 32 (e.g. the plane of photodetector 66 (FIG. 3A)) and projection surface 38 onto which user interface menu image 22 is projected. In the illustrated embodiment, these volume regions include: volume region 82 located between reference surface 70 and a first threshold surface 72, volume region 84 located between threshold surface 72 and threshold surface 74 and volume region 86 located between threshold surface 74 and projection surface 38. Threshold surfaces 72, 74 may be set by controller 30 in relation to projection surface 38 and may be configurable (e.g. user configurable). Reference surface 72 may be set at a distance d1 from (e.g. above) projection surface 38 (or an average height of projection surface 38) and reference surface 74 may be set at a distance d2 from (e.g. above) projection surface 38 (or an average height of projection surface 38). The distances d1 and d2 may be configured, for example, for the height or physical characteristics of practitioner 12. With such an implementation, volume region 82 corresponds to distances greater than d1 from projection surface 38, volume region 84 corresponds to distances between d2 and d1 from projection surface 38 and volume region 86 corresponds to distances less than a distance d2 from projection surface 38.

It will be appreciated that when projection surface 38 is located on a portion 28A of an operating table 28 (FIG. 1), projection surface 38 may comprise an irregular profile (e.g. as opposed to planar or flat as shown in FIG. 3B and/or as opposed to horizontal). In some embodiments, such an irregular profile of projection surface 38 may be taken into account when controller 30 sets threshold levels 72, 74—i.e. threshold levels 72, 74 may have variable profiles across their cross-sections to accommodate for irregularities in projection surface 38 and to maintain distances d1 and d2 generally constant. By way of non-limiting example, surface curvature analysis techniques may be used for this purpose. In some embodiments, this is not necessary and the threshold levels 72, 74 can be set to be constant based on an average of the profile of projection surface 38 (e.g. based on a selection of one or more points on projection surface 38) or based on some other characteristic of, and/or reference associated with, projection surface 38. By way of non-limiting example, in some embodiments, system can set threshold levels 72, 74 relative to the point on projection surface 38 that is closest to TOF imaging device 32 and/or to user interface device 26. For brevity, in the remainder of this description, unless the context indicates otherwise, threshold levels 72, 74 may be described as being relative to projection surface 38 which may mean any relative to any suitable reference corresponding to projection surface 38 (e.g. an average of projection surface 38, a point on projection surface 38 and/or the like). In some embodiments, threshold levels 72, 74 may be used to ascertain gestures of the hand(s) 12A of practitioner 12 and may be used to determine whether to turn on or off projector 34 and/or to select one of the functionalities associated with user interface image sections 50 described above.

Figure 4:
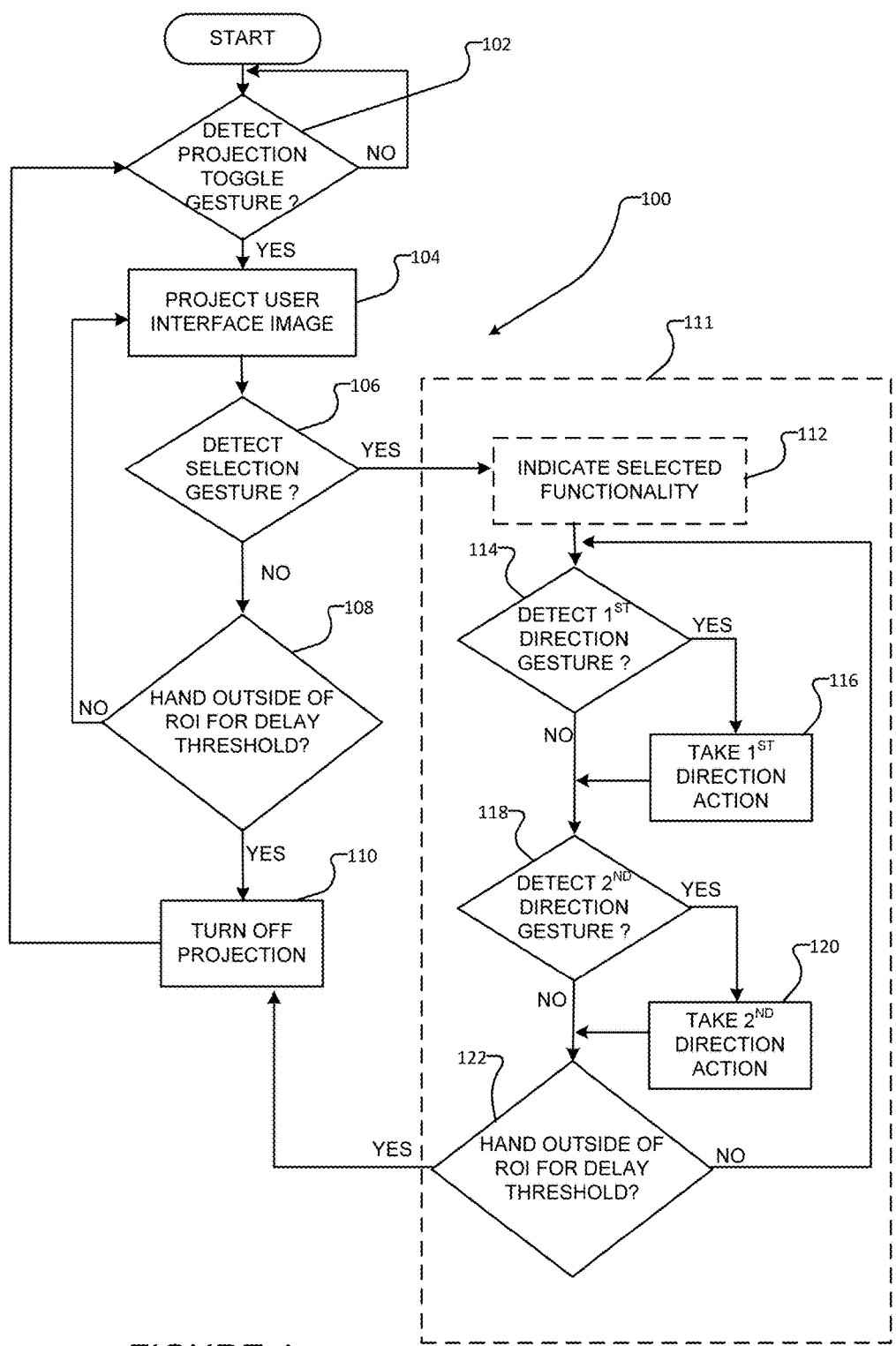
FIG. 4 is a schematic depiction of a method for interpreting gestures made by a medical practitioner using one of their hands according to a particular embodiment.

FIG. 4 is a schematic depiction of a method 100 for interpreting gestures made by practitioner 12 using one of their hands 12A according to a particular embodiment. Method 100 may be performed by user interface device 26. In particular embodiments, method 100 may be performed by controller 30 (in conjunction with TOF imaging system 32 and projector 34). Method 100 of the FIG. 4 embodiment starts in block 102 which involves an inquiry into whether a projection toggle gesture is detected. Block 102 may comprise controller 30 analyzing data received from TOF imaging system 32 to look for a particular projection toggle gesture. In some embodiments, this projection toggle gesture may comprise detecting that the hand 12A of practitioner 12 is first located further from projection surface 38 than threshold 72 (e.g. a location greater than a distance d1 above projection surface 38) and then moves to a location closer to projection surface 38 than threshold 72 (e.g. to a location less than a distance d1 above projection surface 38, to a location less than d1 and greater than d2 above projection surface 38 and/or the like)—see FIG. 3B. In some embodiments, this projection toggle gesture may comprise a side to side movement of the hand 12A of practitioner 12—e.g. a hand wave. In some embodiments, this projection toggle gesture may comprise practitioner 12 holding their hand 12A still with a suitable number of fingers (e.g five fingers) extended. If the block 102 inquiry is negative, then method 100 returns to block 102. If, on the other hand, the block 102 inquiry is positive, then method 100 proceeds to block 104. In some embodiments, a toggle gesture and the block 102 inquiry are not necessary. For example, a conventional switch, remote control activation or the like may be used in the place of a toggle gesture to commence method 100.

Block 104 comprises projecting user interface menu image 22 onto projection surface 38. In block 104, controller 30 may cause projector 34 to project user interface menu image 22 onto projection surface 38, as described elsewhere in this disclosure. Method 100 may then proceed to block 106. Block 106 may involve an inquiry into whether a selection gesture is made. The block 106 selection gesture may comprise selecting a functionality or menu selection associated with one of the user interface image sections 50 in user interface menu image 22 projected in block 104. In some embodiments, the block 106 selection gesture may comprise detecting that the hand 12A of practitioner 12 is located closer to projection surface 38 than threshold 74 (e.g. a location less than a distance d2 above projection surface 38 or even into contact with projection surface 38). Such a gesture may also indicate selection of one among the functionalities and/or menu selections associated with user interface image sections 50. If the block 106 inquiry is positive, the particular one of the functionalities or menu selections selected may, in some embodiments, correspond to the particular one of user interface image sections 50 above which (or most proximate to which) hand 12A is located when it is detected that the hand 12A of practitioner 12 is located closer to projection surface 38 than threshold 74. For example, referring to the FIG. 2 embodiment, if it is detected in block 106 that the hand 12A of practitioner 12 is located between projection surface 38 and threshold 74 and between user interface image section 50D and TOF imaging system 32 (e.g. below threshold 74 and above (or most proximate to) user interface image section 50D), then the particular functionality selected may correspond to the zoom functionality associated with user interface section 50D. As another example corresponding to the FIG. 2 embodiment, if it is detected in block 106 that the hand 12A of practitioner 12 is located between projection surface 38 and threshold 74 and between user interface image section 50A and TOF imaging system 32 (e.g. below threshold 74 and above (or most proximate to) user interface image section 50A), then the particular functionality selected may correspond to the scrolling functionality associated with user interface section 50A. As another example gesture corresponding to the FIG. 2 embodiment, if it is detected that the hand 12A of a practitioner 12 is located between user interface image section 50A and TOF imaging system 32 and the practitioner extends a particular number of fingers (e.g. two fingers), then the particular functionality or menu selection selected may correspond to the scrolling functionality or menu selection associated with user interface section 50A. It will be appreciated that the particular gestures described above are exemplary only and that any gesture(s) discernarble by TOF imaging system 32 in relation to user interface menu image 22. It will be appreciated that where user interface sections 50 correspond to menu selections, then similar gestures may be used to select the particular menu selection corresponding to the particular user interface image section 50 (which may lead to sub-menus to particular actions or functionalities).

If the block 106 inquiry is negative, then method 100 proceeds to block 108. Block 108 may comprise an inquiry into whether the hand 12A of practitioner 12 is moved outside of a region of interest (ROI) for greater than a delay threshold (e.g. a threshold period of time) or whether the hand 12A of practitioner 12 otherwise indicates a toggling gesture. In some embodiments, the block 108 region of interest may comprise a subset of the sensing volume 60 of TOF imaging system 32. In some embodiments, the block 108 region of interest may be correlated with or based on the projected user interface menu image 22. For example, the block 108 region of interest may correspond to some region between TOF imaging system 32 and projected user interface menu image 22 and may have transverse boundaries that are correlated with or based on the size of the projected user interface menu image 22. If the block 108 inquiry is positive (i.e. the hand 12A of practitioner 12 is located outside of the region of interest for greater than a threshold period of time), then method 100 proceeds to block 110 which involves turning off projector 34 (or otherwise discontinuing or not projecting user interface menu image 22 onto projection surface 38). After block 110, method 100 proceeds to block 102—i.e. system 10 returns to its initial state. In some embodiments, when it is first detected that the hand 12A of practitioner 12 is located outside of the region of interest (e.g. prior to the delay threshold), then system 10 may (as a part of block 108) provide a warning indicating that system 10 will return to its initial state after the delay threshold. For example, after detecting that the hand 12A of practitioner 12 is located outside of the region of interest but before the threshold time, controller 30 may cause projector 34 to project a visual indicator that system 10 will soon return to its initial state (e.g. a red circle projected over user interface menu image 22, a flashing and/or highlighted user interface image and/or the like). If, on the other hand, the block 108 inquiry is negative (i.e. the hand 12A of practitioner 12 is located in the region of interest, or is located outside of the region of interest for less than a threshold period of time), then method 100 returns to block 104.

If the block 106 inquiry is positive (e.g. a particular functionality or menu selection associated with a user interface image section 50) is selected by a suitable selection gesture, then method 100 proceeds to block 111. Block 111 of the FIG. 4 embodiment comprises a method for performing a particular functionality (e.g. the functionality selected in block 106) in accordance with a particular embodiment. In some embodiments, as described in more detail below, block 111 may comprise implementing an action corresponding to a menu selection. Once entering the illustrated embodiment of block 111, method 100 commences in optional block 112 which comprises indicating the particular functionality selected as a result of the block 106 inquiry. In particular embodiments, block 112 may comprise causing projector 34 to project an indicator onto the particular one of the selected user interface image sections 50 that is selected in block 106. For example, if the user selects user interface section 50A (corresponding to scrolling—see FIG. 2), then block 112 may comprise projecting an indicator onto user interface image section 50A. By way of example, such an indicator may comprise projecting a circle onto the selected user interface image section 50, a bolding of the selected user interface image section 50, a flashing of the selected user interface image section 50, a highlighting of the selected user interface image section 50 or otherwise drawing attention to the selected user interface image section 50. In some embodiments or situations, in particular if part of the body (e.g. the hand 12A) of practitioner 12 and/or an instrument being used by practitioner 12 might block a portion of projected user interface image menu 22 from appearing on projection surface 38, the selected user interface image section 50 with superimposed indicator (and/or some other portion of the user interface menu image 22), may be projected onto the part of the body (e.g. the hand 12A) of practitioner 12 and/or the instrument being used by practitioner 12. Such projection of the selected user interface image section 50 with superimposed indicator may indicate the selection state. In some embodiments, where the selected user interface image section 50 with superimposed indicator (and/or some other portion of the user interface menu image 22), is projected onto the part of the body (e.g. the hand 12A) of practitioner 12 and/or the instrument being used by practitioner 12, the image portion projected onto the practioner's body or instrument may be adjusted (e.g. scaled and/or warped) based on the distance and/or orientation of the practitioner's body or instrument relative to the projector. This distance and/or orientation may be determined by controller 30 based on data obtained by TOF imaging device 32.

Figure 3C:
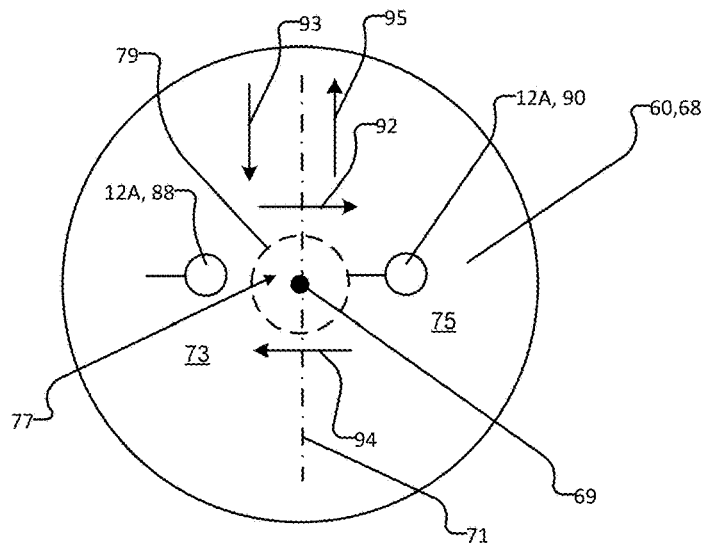

Method 100 then proceeds to block 114 which involves an inquiry into whether a first directional gesture is detected. In some embodiments, directional gestures may comprise movements of the hand 12A of practitioner 12 in one or more directions generally orthogonal to the direction between TOF imaging device 32 and projection surface 38 and/or between projector 34 and projection surface 38 (or having components in such directions). Such directional gestures are illustrated schematically in FIG. 3C. FIG. 3C is a schematic cross-sectional illustration of space 68 of sensor volume 60 of TOF imaging device 32 taken along the line 3C-3C of FIG. 3B. In the exemplary case of the illustrated embodiment of FIG. 3C, if the hand 12A of a practitioner 12 moves in direction 92 (e.g. to location 90 in the schematic illustration of FIG. 3C), then this may be interpreted to be a gesture indicative of movement in a first direction 92. Conversely, if the hand 12A of a practitioner 12 moves in direction 94 (e.g. to location 88 in the schematic illustration of FIG. 3C), then this may be interpreted to be a gesture indicative of movement in a second direction 92. In some embodiments, space 68 may be divided into regions (e.g. by notional lines 71 and 79) and movement between regions may be interpreted as being directional gesture(s). For example, FIG. 3C shows three regions 73, 75, 77 separated by notional lines 71 and 79. In the exemplary case of the illustrated embodiment of FIG. 3C, if the hand 12A of a practitioner 12 is located in a null region 77 bounded by notional line 79, this may be interpreted to mean no directional gesture, but where the hand moves from null region 77 to first direction region 75 (outside of null region 77 and on one side of notional line 71 (the right hand side of line 71 in the schematic illustration of FIG. 3C)), then this may be interpreted to be a gesture indicative of movement in a first direction 92. Conversely, if the hand 12A of a practitioner 12 moves from null region 77 to second direction region 73 (outside of null region 77 and on the opposing side of notional line 71 (the left hand side of line 71 in the schematic illustration of FIG. 3C)), then this may be interpreted to be a gesture indicative of movement in a second direction 94. In some embodiments, other regions may additionally or alternatively be considered to be null regions similar to null region 77 described herein. For example, the region above d1 (FIG. 3B) may be considered to be a null region. In some embodiments, other directional regions (and/or additional directional regions) may be provided.

In some embodiments, the block 114 inquiry may be positive when the hand 12A of a practitioner 12 moves from null region 77 to first direction region 75 (e.g. in direction 92 in the schematic illustration of FIG. 3C), in which case, method 100 proceeds to block 116. Block 116 comprises implementing the action associated with the block 106 selected functionality and the block 114 first direction. In some embodiments, block 116 may comprise implementing functionality that is similar to one direction of the bi-directional functionality associated with the wheel input of a conventional computer mouse. For example, when the block 106 selected functionality comprises scrolling and the block 114 inquiry is positive, then block 116 may involve scrolling through available images in a first direction.

In some embodiments, the block 116 action may occur for the period of time in which the block 114 inquiry is positive and may stop only when the block 114 inquiry becomes negative. For example, in the illustrated embodiment of FIG. 3C, the block 116 action may occur for a period of time in which the hand 12A of practitioner 12 is located outside of null region 77 and in first direction region 75 on one side of notional line 71. If practitioner 12 moves their hand 12A from region 75, back to null region 77 or to second direction region 73, then the block 114 inquiry may become negative and the block 116 action may stop.

In some embodiments, blocks 114 and 116 may comprise logic that facilitates relatively more complex gesture control. Some embodiments may comprise ascertaining a magnitude metric associated with a particular gesture in addition to, or as an alternative to, the directionality of the gesture. For example, a magnitude parameter may be discerned between blocks 114 and 116 of FIG. 4 and may comprise determining an amount (e.g. magnitude metric) that practitioner 12 has moved their hand 12A from null region 77 into first direction region 75, a distance of hand 12A of practitioner 12 from central axis 69 and/or notional line 71 (FIG. 3C), a speed with which practitioner 12 moves their hand 12A from null region 77 to first direction region 75, a movement of the practitioner's hand 12A along some other axis (e.g. in one of directions 93, 95 shown in FIG. 3C or in one of directions 97, 99 shown in FIG. 3B), some combination of these magnitude metrics and/or the like. Such a detected magnitude metric can then be used in block 116, to control a corresponding amount of the associated functionality. For example, where block 116 comprises performing a zoom in action, then the discerned magnitude metric may be used to determine an amount of and/or a speed of zooming in that is performed in block 116—i.e. the amount of and/or speed of zooming may be correlated with, a function of, proportional to and/or otherwise based on the discerned magnitude metric. As another non-limiting example, in the case of scrolling, blocks 114 and 116 may incorporate speed-sensitive gesture control—e.g. so that the speed with which practitioner 12 moves their hand 12A from null-region 77 to first direction region 75 may provide the basis for the corresponding amount of and/or speed of the scrolling action that is taken in the first direction in block 116.

In some embodiments, the magnitude metric ascertained in blocks 114, 116 may comprise a speed-based metric (e.g. how fast is practitioner 12 moving their hand 12A) and/or a position-based metric (e.g. how far is the hand 12A of practitioner 12 from central axis 69 and/or notional line 71). Such ascertained speed-based and/or position-based magnitude metrics can be correlated with (and/or mapped) to corresponding speed-based and/or position-based amounts of functionality. By way of non-limiting example:

- a position-based magnitude metric can be correlated with a position-based amount of corresponding functionality (e.g. the position of hand 12A can be correlated with and/or mapped to a position-based amount of panning or a number of images scrolled through and/or the like);
- a position-based magnitude metric can be correlated with a speed-based amount of corresponding functionality (e.g. the position of hand 12A can be correlated with and/or mapped to a speed of panning or a speed of scrolling through images and/or the like);

a speed-based magnitude metric can be correlated with a position-based amount of corresponding functionality (e.g. the speed of hand 12A can be correlated with and/or mapped to a position-based amount of panning or a number of images scrolled through and/or the like); and/or a speed-based magnitude metric can be correlated with a speed-based amount of corresponding functionality (e.g. the speed of hand 12A can be correlated with and/or mapped to a speed of panning or a speed of scrolling through images and/or the like).

In some embodiments, other additional or alternative magnitude metric(s) may be correlated with (and/or mapped to) other additional or alliterative functionality amounts. In some embodiments, the correlation and/or mapping between magnitude metric(s) and functionality amounts can depend on a particular selected functionality. For example, in some embodiments the panning functionality may correlate and/or map a position-based magnitude metric to a position based panning function, whereas the scrolling functionality may correlate and/or map a position-based magnitude metric to a speed of scrolling.

Additionally or alternatively, in some embodiments, a practitioner may be able to further increase or decrease a magnitude metric by using a suitable gesture sequence. By way of non-limiting example, in some embodiments, this may involve a practitioner 12 moving their hand 12A from null region 77 to first direction region 75 to correspond to a first level of the magnitude metric and then raising/lowering their hand 12A above/below some threshold (e.g. above d1 (FIG. 3B)), drawing their hand 12A back to null region 77 and then repeating the movement from null region 77 to first direction region 75 to cause an increase in the magnitude metric. Other gesture combinations could additionally or alternative be used to increase or decrease a magnitude metric. For example, a practitioner 12 could move their hand from null region 77 into first direction region 75 and may then move their hand up to increase the magnitude metric and down to decrease the magnitude metric (or vice versa).

Additionally or alternatively, in some embodiments, a practitioner may be able to repeat discrete iterations of the block 116 actions using a suitable gesture sequence in a manner similar to rolling from the top to the bottom of a mouse wheel and then lifting a finger to "reset" the finger to the top of the wheel and to repeat scrolling from the top to the bottom. By way of non-limiting example, in some embodiments, this may involve a practitioner 12 moving their hand 12A from null region 77 to first direction region 75 (e.g. outside of null region 77 and to the right (in the illustrated view of FIG. 3C) of notional line 71) to cause a first iteration of block 116 and then raising their hand 12A above some threshold (e.g. above d1 (FIG. 3B)), drawing their hand 12A back to null region 77 and then repeating the movement from null region 77 to first direction region 75 to cause a second iteration of block 116. Gestures other than a practitioner 12 raising their hand 12A above some threshold may be used to "reset" the iterative gesture sequence. For example, a practitioner could flick all five fingers to indicate that they were resetting and then reset their hand back to null region 77. In some embodiments, a specific "reset" gesture may not be required and a repeated sequence of moving back and forth between null region 77 and first direction region 75 may be interpreted to be repeated iterations of a first direction gesture and may cause repeated iterations of block 116, provided that the practitioner does not move their hand 12A into second direction region 73 (e.g. outside of null region 77 and left (in the FIG. 3C view) of notional line 71).

Referring back to FIG. 1, implementing block 116 in accordance with the particular embodiment illustrated in the FIG. 1 embodiment, may comprise controller 30 causing communications interface 36 to communicate with (e.g. send a command to) a workstation 44 (e.g. with a corresponding communication interface 46 associated with workstation 44). As is the case with the illustrated embodiment of FIG. 1, workstation 44 may be located outside of sterile environment 16 (e.g. in a non-sterile region 18). By way of non-limiting example, communications interfaces 36, 46 may comprise suitably configured wired or wireless communications interfaces (e.g. routers) which may communicate with one another over suitable LAN or WAN networks.

Workstation 44 may comprise a suitable software interface 48. Upon receiving a command from user interface device 26, workstation 44 may interact with a memory location 49 (e.g. hospital servers) where medically relevant information is maintained. The interaction between workstation 44 and memory location 49 may (although need not necessarily) be through communications interface 46 and over suitable WAN or LAN networks (not shown). In some embodiments, memory location 49 may be connected to workstation 44 using some other communications protocol. For example, memory location 49 may comprise a hard drive, a USB memory stick an optical disc and/or the like which may be accessible to workstation 44. Memory location 49 may store images and/or other medically relevant information. In response to receiving a command from workstation 44 (corresponding to the command from user interface device 26), memory location 49 may provide suitable medically relevant information to workstation 44 which may in turn provide such information to user interface device 26. In the illustrated embodiment, such information is provided to controller 30 of user interface device 26 which causes display 24 to display this information.

For example, referring to FIG. 1 and to FIG. 4, when the block 106 selected functionality comprises scrolling and the block 114 is positive, then block 116 may involve retrieving images from memory location 49 and displaying a scrolling action (on display 24) through the available images. As another example, when the block 106 selected functionality comprises zooming and the block 114 is positive, then block 116 may involve retrieving more detailed data about a particular image from memory location 49 and displaying a zoom action (on display 49) to zoom in on the particular image. In some embodiments, workstation 44 implements Osirix software which may be part of software interface 48 and which may interact with: picture archiving communication systems (PACS); digital imaging and communications in medicine systems (DICOM), hospital information systems (HIS), radiological information systems (RIS) and/or the like In some embodiments, some of the block 116 actions may not require interaction with memory location 49, as the data for displaying the appropriate image may be already be available at user interface device 26 (e.g. in memory (not shown) accessible to controller 30). In some embodiments, different architectures may be implemented to provide the functionality of block 116. For example, in some embodiments, workstation 44 may communicate directly to display 24 and workstation 44 may, in response to a command received from user interface device 26, cause display 24 to display a particular image without communicating the image back to user interface device 26. As another example, in some embodiments, user interface device 26 may communicate directly with memory location 49, in which case image data may be retrieved directly from memory location 49 by user interface device 26 and workstation 44 may not be required.

Returning again to FIG. 4, if the block 114 inquiry is negative, then method 100 proceeds to block 118 which involves an inquiry into whether a second direction gesture is detected. As discussed above, in some embodiments, directional gestures may comprise movements of the hand 12A of practitioner 12 in one or more directions generally orthogonal to the direction between TOF imaging device 32 and projection surface 38 and/or between projector 34 and projection surface 38 (or having components in such directions). In the exemplary case of the illustrated embodiment of FIG. 3C, if the hand 12A of a practitioner 12 moves from null region 77 to second direction region 73 outside of null region 77 an left (in the FIG. 3C view) of notional line 71 (e. in direction 94 in the schematic illustration of FIG. 3C), then this may be interpreted to be a gesture indicative of movement in a second direction 94. If movement in this second direction is detected in block 118 (i.e. the block 118 inquiry is positive), then method 100 may proceed to block 120.

Block 120 may comprise implementing the action associated with the block 106 selected functionality and the block 118 second direction. In this regard, block 120 may implement functionality having a directionality opposite that of block 116 described above. For example, in some embodiments, block 120 may comprise implementing functionality that is similar to one direction of the bi-directional functionality associated with the wheel input of a conventional mouse. For example, when the block 106 selected functionality comprises scrolling and the block 118 inquiry is positive, then block 120 may involve scrolling through available images in a second direction (opposed to the direction of block 116). With the exception of the directionality of the command, implementing blocks 118 and 120 may comprise any of the techniques described above in connection with blocks 114 and 116.

If the block 118 inquiry is negative or block 120 concludes, then method 100 may proceed to block 122. Block 122 involves an inquiry similar to that of block 108 into whether the hand 12A of practitioner 12 is moved outside of a region of interest (ROI) for greater than a delay threshold (e.g. a threshold period of time). The block 122 inquiry may be implemented using techniques similar to those discussed above in connection with block 108. If the block 122 inquiry is positive (i.e. the hand 12A of practitioner 12 is located outside of the region of interest for greater than a threshold period of time), then method 100 proceeds to block 110 which involves turning off projector 34 (or otherwise discontinuing or not projecting user interface menu image 22 onto projection surface 38). After block 110, method 100 proceeds to block 102—i.e. system 10 returns to its initial state. In some embodiments, when it is first detected that the hand 12A of practitioner 12 is located outside of the region of interest (e.g. prior to the delay threshold), then system 10 may (as a part of block 122) provide a warning indicating that system 10 will return to its initial state after the delay threshold. For example, after detecting that the hand 12A of practitioner 12 is located outside of the region of interest but before the threshold time, controller 30 may cause projector 34 to project a visual indicator that system 10 will soon return to its initial state (e.g. a red circle projected over user interface menu image 22, a flashing and/or highlighted user interface image and/or the like). If, on the other hand, the block 122 inquiry is negative (i.e. the hand 12A of practitioner 12 is located in the region of interest, or is located outside of the region of interest for less than a threshold period of time), then method 100 returns to block 114.

Figure 6:
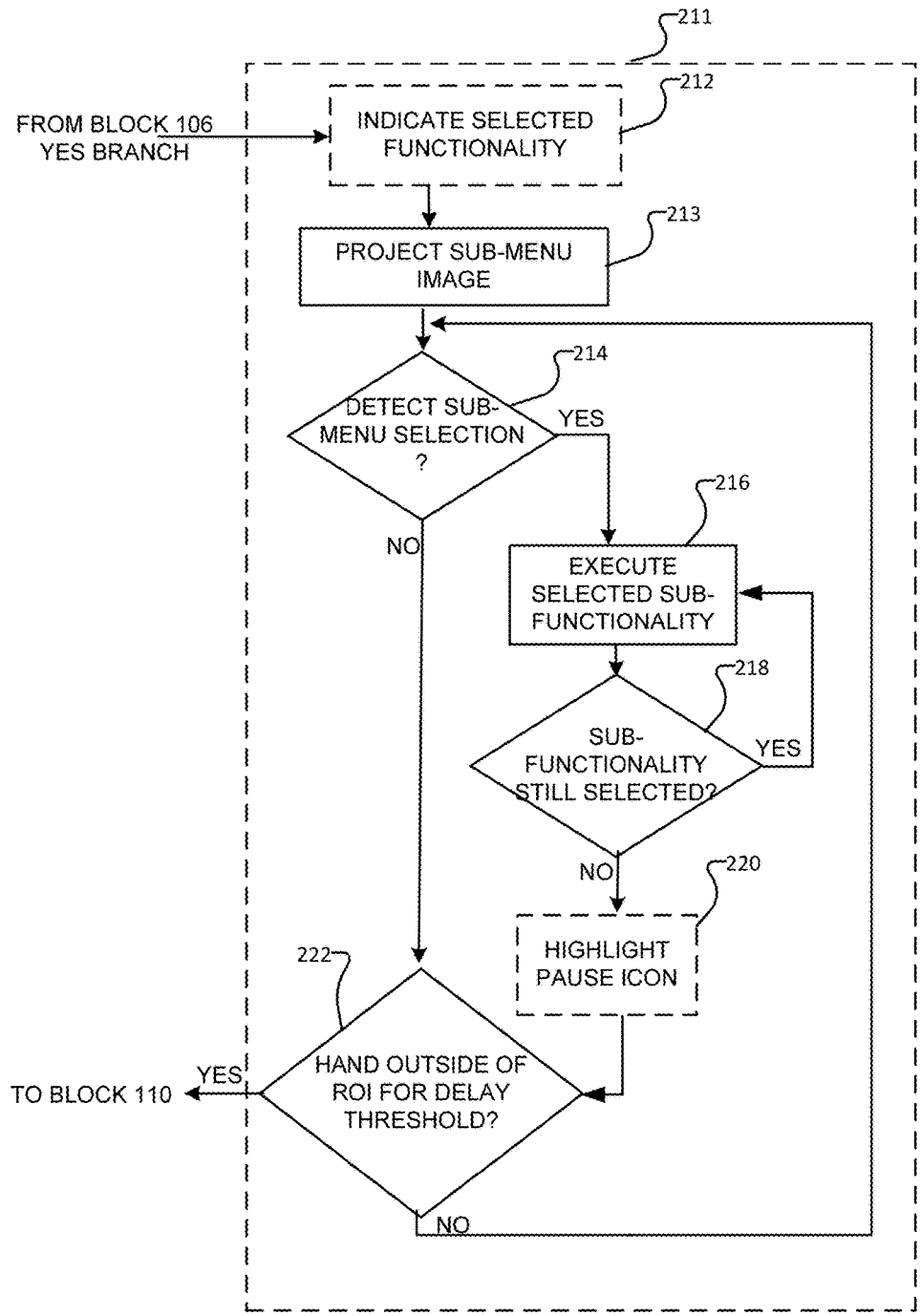
FIG. 6 is a schematic diagram of a method 211 which may be used to implement a portion of the FIG. 4 method according to particular embodiment.

FIG. 6 is a schematic diagram of a method 211 which may be used in addition to and/or in the place of block 111 in the FIG. 4 method 100 according to a particular embodiment. Like the FIG. 4 block 111, the FIG. 6 method 211 comprises a method for performing a particular functionality (e.g. the functionality selected in block 106) in accordance with a particular embodiment. In many respects, method 211 of FIG. 6 is similar to block 111 described elsewhere herein. Consequently, for brevity, this description focuses on the differences between method 211 and block 111 and those skilled in the art will appreciate where the techniques of block 111 described elsewhere herein may be used in method 211. Method 211 commences when the block 106 inquiry (see FIG. 4) is positive. Method 211 commences in optional block 212 which comprises indicating the particular functionality selected as a result of the block 106 inquiry. Block 212 may be substantially similar to block 112 described above.

Figure 7:
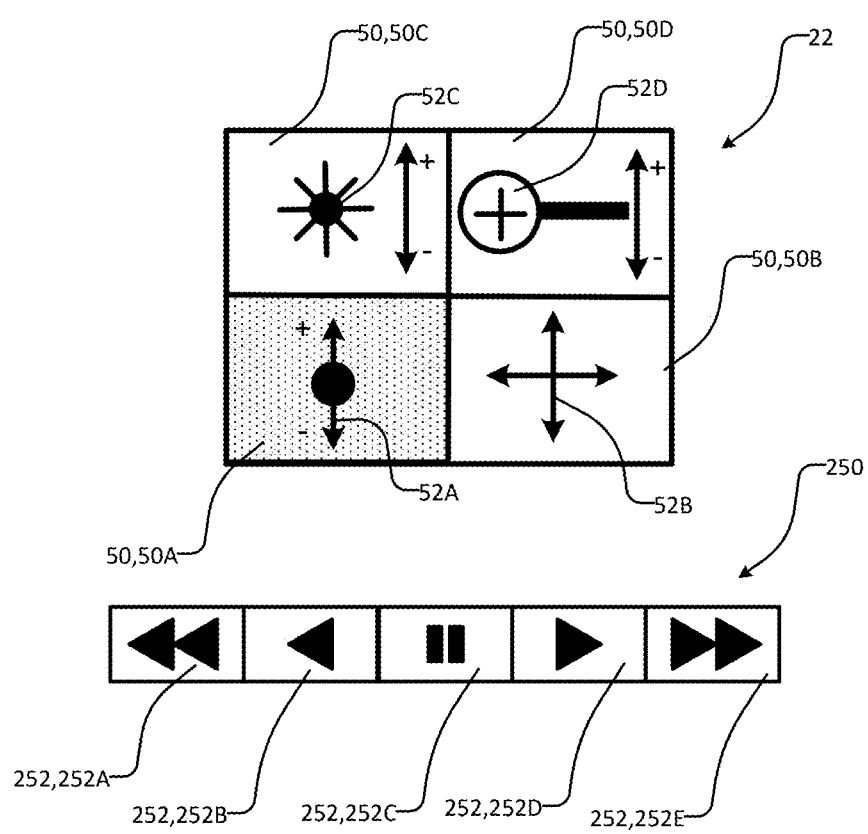
FIG. 7 is a is a schematic depiction of a user interface menu image and a user interface sub-menu image which may be used in the FIG. 6 method according to particular embodiments.

Method 211 then proceeds to block 213, which involves controller 30 causing projector 34 projecting a sub-menu image 250 onto projection surface 38. The projection of sub-menu image 250 onto projection surface 38 may (except for the content of the projection) be substantially similar to the projection of user interface menu image 22 onto projection surface 38. FIG. 7 shows an example sub-menu image 250 which may be projected onto projection surface 38 in block 213 according to a particular embodiment. Sub-menu image 250 comprises a plurality of sub-menu image sections 252 (individually, sub-menu image sections 252A, 252B, 252C, 252D, 252E). Sub-menu image sections 252 may be selected using gestures (e.g. gestures of the hand(s) 12A of practitioner 12) in a manner similar to any of the techniques described herein for selection of user interface image sections 50. In the illustrated embodiment shown in FIG. 7, user interface menu image 22 is projected simultaneously with sub-menu image 250 and user interface menu image 22 is shown with the scroll functionality (user interface image section 50A) highlighted, although neither of these features are necessary. In some embodiments, user interface menu image 22 is not displayed during method 211. In some embodiments, user interface menu image 22 is displayed during method 211, but is shown with decreased size or in some other way which allows sub-menu image 250 to be emphasized relative to user interface menu image 22. In some embodiments, only a portion of user interface menu image 22 (e.g. an icon corresponding to selected one of user interface image sections 50) is displayed during method 211.

It can be seen that sub-menu image 250 of the FIG. 7 embodiment includes sub-menu image sections 252A (corresponding to high magnitude/speed left functionality), 252B (corresponding to a low magnitude/speed left functionality), 252C (corresponding to a pause functionality), 252D (corresponding to low magnitude/speed right functionality) and 252E (corresponding to high magnitude/speed right functionality). As discussed above, the functionalities corresponding to each of sub-menu image sections can be selected using any of the gesture-based techniques described herein for selection of user interface image sections 50. In block 214, method 211 involves an inquiry as to whether practitioner 12 has used a gesture to select any of the sub-menu image sections 252 and the corresponding functionality. If the block 214 inquiry is negative, then method 211 proceeds to block 222 which is substantially similar to block 122 described above in connection with FIG. 4 and block 111. If the block 214 inquiry is positive, then method 211 proceeds to block 216 which involves system 10 implementing the block 106 selected functionality with the block 214 selected sub-menu directionality and magnitude/speed. For example, in the case of the FIG. 7 example, the block 106 selected functionality is a scroll functionality (corresponding to user interface menu section 50A). If practitioner 12 uses a gesture to select sub-menu image section 252E in block 214, then, in block 216, system 10 may cause a scroll right or up (directionality) with a relatively rapid scroll rate (high magnitude) of the image displayed on display 24 (FIG. 1). In contrast, if practitioner 12 uses a gesture to select sub-menu image section 252B in block 214, then, in block 216, system 10 may cause a scroll left or down (directionality) with a relatively low scroll rate (low magnitude) of the image displayed on display 24. The methods and techniques that are used to implement block 216 of method 211 may be similar to any of those described herein, for example, in connection with implementing the actions of blocks 116 and/or 120 of FIG. 4.

In block 218, method 211 involves checking whether the block 214 sub-menu image section 252 remains selected. If practitioner 12 is continuing to select a particular sub-menu image section 252 and its corresponding functionality (e.g. by leaving their hand 12A over the particular sub-menu image section 252 or otherwise using a gesture to select the particular sub-menu image section 252), then the block 218 inquiry is positive and method 211 loops back to block 216 where system 10 continues to implement the corresponding action. If practitioner 12 discontinues the selection of a particular sub-menu image section 252 and its corresponding functionality (e.g. by moving their hand 12A away from sub-menu image 250 or otherwise using a gesture to de-select the particular sub-menu image section 252), then the block 218 inquiry is negative and method 211 proceeds to optional block 220. In optional block 220, system 10 may highlight the "pause" icon shown in sub-menu image section 252C of the FIG. 7 embodiment. The techniques used for highlighting the pause icon in optional block 220 may be similar to any of those described herein for indicating the selected functionality in optional block 112. A similar optional block for highlighting the pause icon may be located between the block 214 NO branch and block 222. Method 211 may eventually reach block 222 which provides functionality similar to that of block 122 described elsewhere herein.

It will be appreciated by those skilled in the art that the functionality of method 100 (implemented using block 111 and/or method 211) provides directional actions in two opposing directions (e.g. the actions associated with blocks 116 and 120). In some embodiments, different numbers of directionalities may be provided for particular selected actions. For example, in the FIG. 2 user interface menu image 22, one of the user interface image (sections 50B) corresponds to panning which may comprise panning in more than two opposing directions. In this case, method 100 of FIG. 4 may be modified by providing additional inquiries similar to those of blocks 114, 118, but for additional (e.g. third and fourth) directions and corresponding additional actions similar to those of blocks 116, 120, but for such additional directions. In such embodiments, additional directional zones may be provided in the schematic illustration of FIG. 3C. Similarly, additional sub-menu image sections 252 can be used in method 211 to provide such additional directions.

For the purposes of selection of user interface image sections 50 and their corresponding functionalities, system 10 provides menu-like interaction for practitioner 12. It will be appreciated that in some embodiments, "drill down" type menu interaction may be provided, where the "functionality" associated with a particular user interface image section 50 is to cause controller 30 to cause projector 34 to display a user interface sub-image, where the user interface sub-image comprises a new set of user interface sub-image image sections with corresponding graphical and/or textual icons and corresponding functionalities. It will be appreciated that multiple levels of sub-menus may be implemented in this fashion. Method 100 may be modified to provide such functionality, for example by providing multiple levels of inquiry similar to that of block 106 and, at each successive detection of a selection gesture, displaying a corresponding user interface sub-image comprises a new set of user interface image sections.

In some embodiments, the directionality of the actions taken as a part of method 100 are not necessary. For example, it might be sufficient to select one particular one of the functionalities associated with one of the user interface image sections 50 or one of the user interface sub-image sections. In such embodiments, block 111 and/or method 211 may be replaced by or augmented (e.g. by addition of) a block which involves performing the selected action, without considering directionality. By way of non-limiting example, in some embodiments, a user interface sub-image section may be associated with the functionality of playing back the current video clip or animating a sequence of the next number (e.g. 300) images into a video clip and playing back same. If such a user interface sub-image section is selected, then block 111 of method 100 may comprise playing back the video clip without any inquiry into directionality and then proceeding to block 122 after the video clip is played back.

As discussed above, controller 30 causes projector 34 to project user interface menu image 22 onto projection surface 38 which is located in sterile environment 16 and is suitable for being viewed and interacted with by medical practitioner 12. In some embodiments, projection surface 38 may comprise the generally horizontal surface of a portion 28A of operating table 28 on which patient 14 is located. Medical practitioner 12 may interact with system 10 by making gestures using one of (or both of) their hands 12A in space 68 between portion 28A of operating table 28 and user interface device 26 and such gestures may be interpreted based on the location of the practitioner's hand 12A relative to the projected user interface menu image 22 and/or relative to the projection surface 38 on which the user interface menu image 22 is projected. In some embodiments, system 10 may adjust the size of projected user interface menu image 22 (based on data acquired by the TOF imaging system 32) so that projected user interface menu image 22 fits on the portion 28A of operating table 28 (e.g. without crossing over the operating table edges). For example, controller 30 may interpret data captured by TOF imaging system 32 to locate the edges of operating table 28 (e.g. by the sharp changes in height between operating table 28 and the floor on the other side of the edges). Controller 30 may then cause projector 34 to adjust the size of user interface menu image 22 (as projected) to fit onto portion 28A of operating table 28.

Although generally horizontal, in embodiments where projection surface 38 comprises a portion 28A of operating table 28, projection surface 38 may be irregular (e.g. non-planar or generally, but not perfectly, horizontal). This irregularity of projection surface 38 may be due to the presence of the patient's body, the state of any projection surface (e.g. operating table) coverings, the presence of medical instruments and/or the like. In some embodiments, system 10 may compensate the projected used interface image 22 based on detected irregularity of projection surface 38. For example, controller 30 may determine a 3D profile of projection surface 38 based on information acquired by TOF imaging system 32 and may use such a 3D profile to cause projector 34 to adjust the projection of user interface menu image 22 to compensate for the surface irregularity. In some embodiments, system 10 may adjust projected user interface image to compensate for reflectivity and/or color of projection surface 38. For example, controller 30 may estimate the reflectivity or color of projection surface 38 based on data acquired by the TOF imaging system 32 or by some other suitable imaging system (not shown), such as a color camera or the like. Controller 30 may then use this information to cause projector 34 to adjust the projection of user interface menu image 22 to compensate for the reflectivity and/or color of projection surface 38.

Figure 5A:
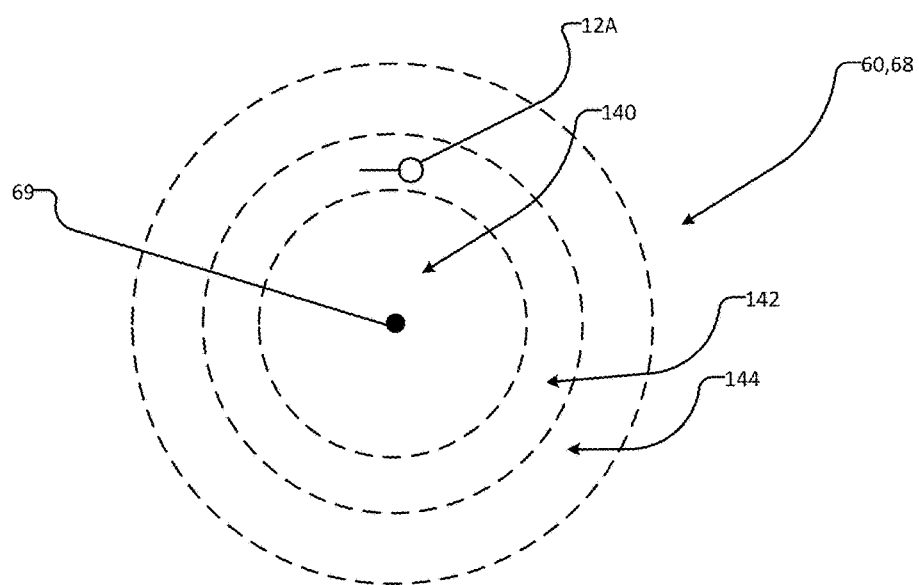
FIGS. 5A and 5B respectively represent regions of interest and look up table plots that may be used to adjust the integration time of a TOF imaging system (or other 3-D optical imaging system) in some embodiments.

In some embodiments, it may be desirable to adjust the integration time of TOF imaging system 32 to compensate for irregular illumination of its sensing volume 60 by its radiation source(s) 64 (see FIG. 3A). Adjusting the integration time of TOF imaging system 32 corresponds to adjusting the amount of radiation that is received at detector 66. For this purpose, space 68 may be notionally divided into three cross-sectional regions of interest 140, 142, 144 as shown in FIG. 5A and as delineated, for example, by suitable radial coordinate thresholds as shown in dashed lines in FIG. 5A. In the illustrated embodiment of FIG. 5A, central region 140 is circular in cross-section, and regions 142, 144 are annular in cross-section and these regions are concentric with axis 69. It will be appreciated that in other embodiments, other numbers and/or configurations of regions of interest may be used. In some embodiments, system 10 may locate or track the 3D location of the hand 12A of practitioner 12 and may compensate the integration time of TOF imaging system 32 based on: the region of interest (e.g. region 140, 142 or 144) where hand 12A is located; and the distance (e.g. height) h along axis 69 between hand 12A and TOF imaging system 32 (or between hand 12A and a reference location (e.g. the coordinate system origin) associated with TOF imaging system 32. An exemplary hand 12A located in region 142 is shown in FIG. 5A. An exemplary distance h along axis 69 between hand 12A and a reference location associated with TOF imaging system 32 is shown in FIG. 3A.

Figure 5B:
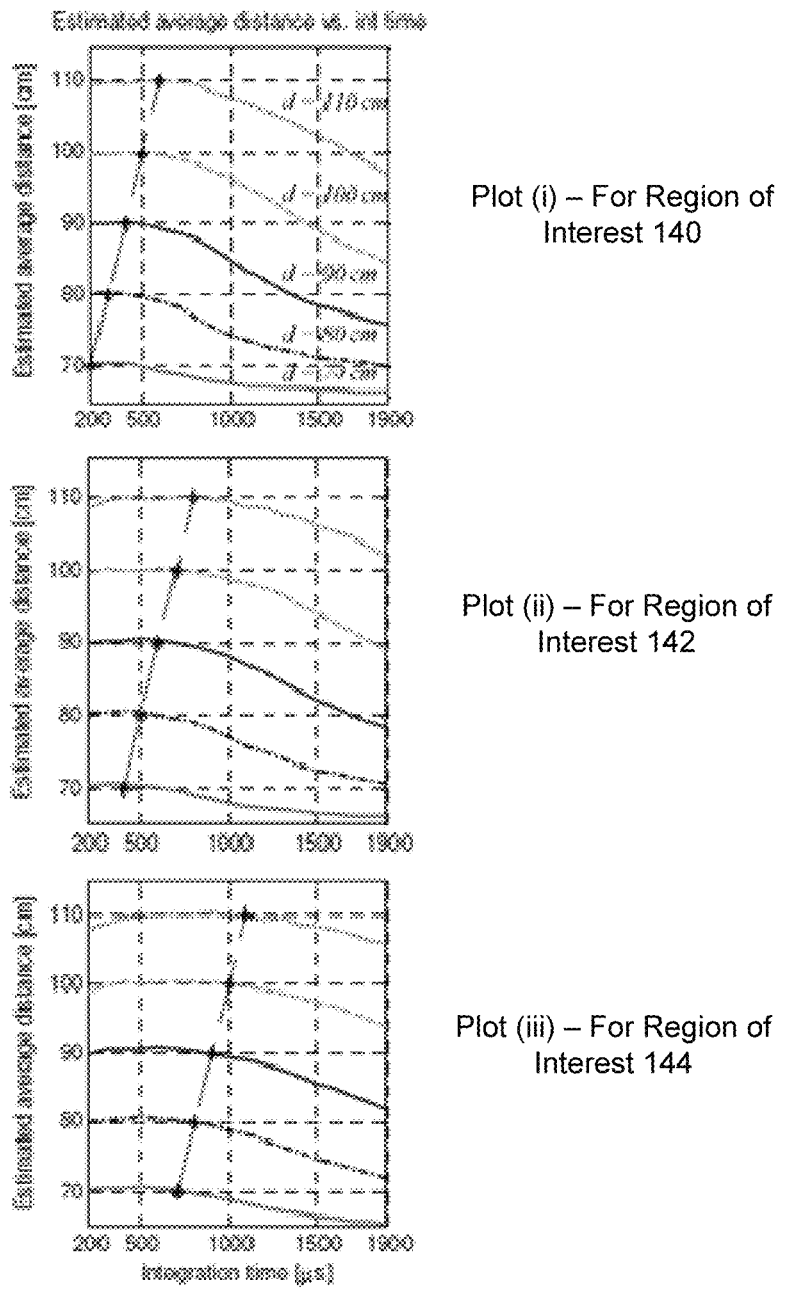

In some embodiments, these two inputs may be used as the basis for determining a suitable integration time based on one or more look up tables. Suitable plots which may be used as the basis for such look up tables are provided in FIG. 5B. In particular, the region of interest (e.g. 140, 142, 144) where hand 12A is determined to be located may be used as the basis for selecting between the look-up tables of plots (i) corresponding to central region of interest 140, (ii) corresponding to annular region of interest 142; and (iii) corresponding to annular region of interest 144. Once the plot is selected, then the particular curve that is used to provide the integration time may be selected based on the distance h of hand 12A from the reference location associated with TOF imaging system 32—i.e. the y-axis of each plot provides a distance h and the x-axis of each plot provides a corresponding integration time.

Some of the embodiments described herein employ relatively small movements of the hand 12A. This may be advantageous in cases where there are a relatively large number of individuals present in sterile environment 16 (FIG. 1) and/or where medical practitioner 12 is wearing heavy lead gear during a procedure. Some embodiments described herein employ a ceiling mounted system which projects user interface image onto an upwardly facing, generally horizontal surface. This orientation may be advantageous as it may not require practitioner 12 to look up from the patient and face a monitor with a vertical screen across operating table 28 to effect gestures and may avoid occlusion of the TOF imaging system by other objects or tools in sterile environment 16 and may generally avoid interference with other objects or tools in sterile environment 16.

Certain implementations of the invention comprise computers and/or computer processors which execute software instructions which cause the computers and/or processors to perform a method of the invention. For example, one or more processors in a computer system may implement data processing steps in the methods described herein by executing software instructions retrieved from a program memory accessible to the processors. The invention may also be provided in the form of a program product. The program product may comprise any medium which carries a set of computer-readable signals comprising instructions which, when executed by a data processor, cause the data processor to execute a method of the invention. Program products according to the invention may be in any of a wide variety of forms. The program product may comprise, for example, physical (non-transitory) media such as magnetic data storage media including floppy diskettes, hard disk drives, optical data storage media including CD ROMs, DVDs, electronic data storage media including ROMs, flash RAM, or the like. The instructions may be present on the program product in encrypted and/or compressed formats.

Where a component (e.g. a software module, controller, processor, assembly, device, component, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

While a number of exemplary aspects and embodiments are discussed herein, those of skill in the art will recognize certain modifications, permutations, additions and sub-combinations thereof. For example:

Medically relevant information which may be displayed by system 10 on display 24 may generally include any type of information. In some embodiments, this medically relevant information may comprise images of patient 14 on which the procedure is being performed. Such images can be acquired prior to or during the procedure and, in general, there is no limitation on the type of technology used to acquire such images. By way of non-limiting example, such images maybe procured by X-ray, computer tomography (CT) scan, magnetic resonance imaging (MRI), ultrasound, endoscopy, elastography, thermography, positron emission tomography and/or the like. In some embodiments, some such images may be grouped together to provide video clips. As used herein, images should be understood to include video clips.

In the FIG. 4 method 100, the gestures used to effect directionality, magnitude and/or speed of a particular functionality are not limited to those described above and may comprise any suitable gestures discernable by TOF imaging system 32. By way of non-limiting example, the speed of a scroll functionality can be made to scroll faster if practitioner 12 moves their hand 12A in one direction relation to TOF imaging system 32 and made to scroll slower if practitioner 12 moves their hand 12A in the opposite direction relation to TOF imaging system 32.

In some of the embodiments described above, distances and thresholds used by system 10 to discern gestures or otherwise are described with respect to projection surface 38. In some embodiments, system 10 may be configured to discern the bed 28 from other objects in the sensing volume of TOF imaging system 32 and may set such thresholds and distances relative to a surface of (or an estimate of a surface of) bed 28 in addition to in the alternative to setting such thresholds and distances relative to projection surface 38.

Embodiments are described herein as interpreting gestures made by practitioner 12 using his or her hand 12A. Use of the hand 12A is not explicitly necessary. System 10 may be configured to interpret 3D gestures made by practitioner 12 using other objects, such as an instrument being held by practitioner 12, another limb of practitioner 12, the fingers of practitioner 12 and/or the like.

In some embodiments, controller 30 may discern (with the assistance of 3D images from TOF imaging system 32) other gestures (e.g. finger based gestures) which do not involve interaction of practitioner 12 with user interface menu image 22. When so discerned, such other gestures may be used to provide addition or alternative functionality.

In the embodiments described above, a gesture vocabulary based on palm down motions is defined and recognized by system 10. In some embodiments, additions or other alterations can be made to this gesture vocabulary.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A system for permitting a medical practitioner to interact with an image comprising medically relevant information during a medical procedure, the system comprising:
   a projector for projecting a user interface menu image onto a projection surface, the user interface menu image comprising a plurality of user interface image sections, each user interface image section occupying a different portion of the user interface menu image and associated with a corresponding functionality;
   a three-dimensional optical imaging system for capturing three-dimensional location information for objects in a sensing volume which includes the projection surface;
   a controller connected to receive the three-dimensional location information from the three-dimensional optical imaging system and configured to:
   interpret the three-dimensional location information to estimate a location of a hand of the practitioner in a space between the three-dimensional optical imaging system and the projection surface; and
   interpret the location of the hand of the practitioner to be a selection of a particular one of the plurality of user interface image sections and the corresponding functionality based only on the location of the hand relative to the particular one of the user interface image sections and comparison of the location of the hand to one or more threshold surfaces defined by distances from the projection surface; and
   a display for displaying an image comprising medically relevant information;
   wherein the controller is further configured, based on the location information captured by the three-dimensional optical imaging system and after interpreting the location of the hand of the practitioner to be the selection of the particular one of the plurality of user interface image sections and the corresponding functionality, to interpret one or more gestures comprising movements made by the hand of the practitioner to indicate one or more corresponding commands to manipulate the displayed image comprising medically relevant information;
   wherein the controller is configured to interpret the one or more gestures to indicate one or more corresponding commands by:
   causing the projector to project a sub-menu image onto the projection surface, the sub-menu image comprising a plurality of sub-menu interface sections, each sub-menu interface section occupying a different portion of the sub-menu image and associated with a corresponding one of the one or more corresponding commands; and
   interpreting the one or more gestures to comprise a selection of a particular one of the sub-menu interface sections and a corresponding one of the one or more corresponding commands based on a location of the one or more gestures relative to the particular one of the sub-menu interface sections; and
   wherein the controller is configured to cause the display to effect the corresponding one of the one or more corresponding commands to thereby manipulate the displayed image comprising medically relevant information in accordance with the corresponding one of the one or more corresponding commands; and
   wherein the one or more gestures comprises moving one of the practitioner's hands to a location that is within a first threshold distance of the projection surface, wherein the first threshold distance is determined relative to at least one of: a reference point associated with the projection surface, the reference point comprising an average of a plurality of points on the projection surface; and an estimate of the location of the projection surface based on detection of a bed in the sensing volume.

2. A system according to claim 1 wherein the projector, the three-dimensional optical imaging system and the display are located in a sterile environment in which the medical procedure is being performed.

3. A system according to claim 1 wherein the projection surface comprises at least one of: a portion of an operating table on which the patient undergoing the medical procedure is located; and a generally horizontal surface of a side table in a room in which the medical procedure is being performed.

4. A system according to claim 1 wherein the controller is connected to the projector and configured to switch the projector from an off state, where the projector does not project the user interface menu image onto the projection surface, to an on state, where the projector does project the user interface menu image onto the projection surface, based at least in part on a detection, prior to switching the projector to the on state, that the hand of the practitioner is located at a toggle position in the sensing volume, the toggle position less than a threshold distance away from the projection surface.

5. A system according to claim 1 wherein the controller is configured to interpret the location of the hand of the practitioner to be the selection of the particular one of the plurality of use interface image sections and the corresponding functionality based on at least one of: a location of the hand above the particular one of the user interface image sections; and a proximity of the hand to the particular one of the user interface image sections.

6. A system according to claim 1 wherein the controller is configured to interpret the one or more gestures to comprise the selection of the particular one of the sub-menu interface sections and the corresponding one of the one or more corresponding commands based on at least one of: the location of the one or more gestures above the particular one of the sub-menu interface sections; and a proximity of the one or more gestures to the particular one of the sub-menu interface sections.

7. A system according to claim 1 wherein the one or more corresponding commands comprise: a zoom in command for zooming into an image displayed on the display and a zoom out command for zooming out of an image displayed on the display; and panning in various directions about an image displayed on the display.

8. A system according to claim 1 wherein the one or more corresponding commands comprise a scroll through images to be displayed on the display in a first direction and a scroll through images to be displayed on the display in a second direction.

9. A system according to claim 1 wherein the one or more corresponding commands comprises a first directional command and a second directional command in a direction opposing the first directional command and wherein the first directional command is associated with a first gesture in a first direction and the second directional command is associated with a second gesture in a second direction, the first and second directions generally opposed to one another.

10. A system according to claim 9 wherein the controller is configured, based on the location information captured by the three-dimensional optical imaging system, to determine a magnitude metric associated with the first gesture based on at least one of an amount of movement associated with the gesture in the first direction, a location of the gesture in the first direction and a speed of the gesture in the first direction and wherein the controller is configured to cause the display to effect those one or more corresponding commands on the medically relevant information displayed on the display based on the magnitude metric.

11. A system according to claim 1 wherein each of the one or more corresponding commands comprises a directionality and a magnitude metric and wherein the controller is configured to cause the display to effect the corresponding one of the one or more corresponding commands on the medically relevant information displayed on the display based on the directionality and the magnitude metric of the corresponding one of the one or more corresponding commands.

12. A system according to claim 1 wherein the controller is configured, after interpreting the location of the hand of the practitioner to be the selection of the particular one of the plurality of user interface image sections and the corresponding functionality, to cause the projector to project an indication, in the user interface menu image, that the particular one of the plurality of user interface image sections and the corresponding functionality were selected.

13. A system according to claim 1 wherein the projection surface comprises an irregular surface profile and wherein the controller is configured, based on the location information captured by the three-dimensional optical imaging system, to: cause the projector to adjust the projection of the user interface menu image to compensate for the irregular surface profile of the projection surface; and create a model of the irregular surface profile of the projection surface and to cause the projector to adjust the projection of the user interface menu image based on the model; wherein the irregular surface profile of the projection surface comprises one or more of: irregularities caused by the presence of a patient's body; irregularities caused by the presence of operating table coverings; and irregularities caused by the presence of one or more medical instruments.

14. A system according to claim 1 wherein the controller is configured to cause the display to display a particular image comprising medically relevant information from among a plurality of images comprising medically relevant information based at least in part on the selection of the particular one of the plurality of user interface sections.

15. A system according to claim 1 wherein the controller is configured to adjust the projection of the user interface menu image based on measured data indicative of at least one of: a reflectivity of the projection surface; and a color of the projection surface.

16. A method for permitting a medical practitioner to interact with an image comprising medically relevant information during a medical procedure, the method comprising:
projecting a user interface menu image onto a projection surface, the user interface menu image comprising a plurality of user interface image sections, each user interface image section occupying a different portion of the user interface menu image and associated with a corresponding functionality;
capturing three-dimensional location information for objects in a sensing volume which includes the projection surface; interpreting the three-dimensional location information to estimate a location of a hand of the practitioner in the sensing volume;
interpreting the location of the hand of the practitioner to be a selection of a particular one of the plurality of user interface sections and the corresponding functionality based only on the location of the hand relative to the particular one of the user interface image sections and comparison of the location of the hand to one or more threshold surfaces defined by distances from the projection surface; and
causing a display to display an image comprising medically relevant information;
based on the captured three-dimensional location information and after interpreting the location of the hand of the practitioner to be the selection of the particular one of the plurality of user interface image sections and the corresponding functionality, interpreting one or more gestures comprising movements made by the hand of the practitioner to indicate one or more corresponding commands to manipulate the displayed image comprising medically relevant information;
wherein interpreting the one or more gestures to indicate one or more corresponding commands comprises:
projecting a sub-menu image onto the projection surface, the sub-menu image comprising a plurality of sub-menu interface sections, each sub-menu interface section occupying a different portion of the sub-menu image and associated with a corresponding one of the one or more corresponding commands; and interpreting the one or more gestures to comprise a selection of a particular one of the sub-menu interface sections and a corresponding one of the one or more corresponding commands based on a location of the one or more gestures relative to the particular one of the sub-menu interface sections; and causing the display to effect the corresponding one of the one or more corresponding commands to thereby manipulate the displayed image comprising medically relevant information in accordance with the corresponding one of the one or more corresponding commands; and wherein the one or more gestures comprises moving one of the practitioner's hands to a location that is within a first threshold distance of the projection surface, wherein the first threshold distance is determined relative to at least one of: a reference point associated with the projection surface, the reference point comprising an average of a plurality of points on the projection surface; and an estimate of the location of the projection surface based on detection of a bed in the sensing volume.

17. A system for performing a surgical procedure, the system comprising:

a projector for projecting a user interface menu image onto a projection surface, the user interface menu image comprising a plurality of user interface image sections, each user interface image section occupying a different portion of the user interface menu image and associated with a corresponding functionality; and a three-dimensional optical imaging system for capturing three-dimensional location information for objects in a sensing volume which includes the projection surface;

a controller connected to receive the three-dimensional location information from the three-dimensional optical imaging system and configured to:

interpret the three-dimensional information to estimate a location of a hand of the practitioner in a space between the three-dimensional optical sensor and the projection surface; and interpret the location of the hand of the practitioner to be a selection of a particular one of the plurality of user interface image sections and the corresponding functionality based only on the location of the hand relative to the particular one of the user interface image sections and comparison of the location of the hand to one or more threshold surfaces defined by distances from the projection surface; and a display for displaying an image comprising medically relevant information;

wherein the controller is further configured, based on the location information captured by the three-dimensional optical imaging system and after interpreting the location of the hand of the practitioner to be the selection of the particular one of the plurality of user interface image sections and the corresponding functionality, to interpret one or more gestures comprising movements made by the hand of the practitioner to indicate one or more corresponding commands to manipulate the displayed image comprising medically relevant information;

wherein the controller is configured to interpret the one or more gestures to indicate one or more corresponding commands by:

causing the projector to project a sub-menu image onto the projection surface, the sub-menu image comprising a plurality of sub-menu interface sections, each sub-menu interface section occupying a different portion of the sub-menu image and associated with a corresponding one of the one or more corresponding commands; and interpreting the one or more gestures to comprise a selection of a particular one of the sub-menu interface sections and a corresponding one of the one or more corresponding commands based on a location of the one or more gestures relative to the particular one of the sub-menu interface sections; and wherein the controller is configured to cause the display to effect the corresponding one of the one or more corresponding commands to thereby manipulate the displayed image comprising medically relevant information in accordance with the corresponding one of the one or more corresponding commands; and wherein the one or more gestures comprises moving one of the practitioner's hands to a location that is within a first threshold distance of the projection surface, wherein the first threshold distance is determined relative to at least one of: a reference point associated with the projection surface, the reference point comprising an average of a plurality of points on the projection surface; and an estimate of the location of the projection surface based on detection of a bed in the sensing volume.

* * * * *